(12) United States Patent
Mahfouz et al.

(10) Patent No.: US 10,662,437 B2
(45) Date of Patent: May 26, 2020

(54) METHOD OF INHIBITING PLANT VIRUS PATHOGEN INFECTIONS BY CRISPR/CAS9-MEDIATED INTERFERENCE

(71) Applicant: King Abdullah University of Science and Technology, Thuwal (SA)

(72) Inventors: Magdy Mahmoud Mahfouz, Thuwal (SA); Zahir Ali, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 72 days.

(21) Appl. No.: 15/575,749

(22) PCT Filed: May 18, 2016

(86) PCT No.: PCT/IB2016/052918
§ 371 (c)(1),
(2) Date: Nov. 20, 2017

(87) PCT Pub. No.: WO2016/185411
PCT Pub. Date: Nov. 24, 2016

(65) Prior Publication Data
US 2019/0106706 A1 Apr. 11, 2019

Related U.S. Application Data

(60) Provisional application No. 62/162,856, filed on May 18, 2015.

(51) Int. Cl.
*C12N 15/82* (2006.01)

(52) U.S. Cl.
CPC ..... *C12N 15/8283* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 9,777,040 B2 * | 10/2017 | Sera | A01N 59/16 |
| 2004/0026114 A1 | 12/2004 | Fauquet et al. | |
| 2015/0089686 A1 | 3/2015 | Fellers et al. | |
| 2016/0237451 A1 * | 8/2016 | Voytas | C12N 15/8283 |

FOREIGN PATENT DOCUMENTS

| | | |
|---|---|---|
| WO | 2011/155426 | 12/2011 |
| WO | 2015/048707 | 4/2015 |

OTHER PUBLICATIONS

Search Report and Written Opinion for PCT/IB2016/052918 dated Jul. 12, 2016.
Baltes, et al., "Conferring resistance to geminiviruses with the CRISPR-Cas prokaryotic immune system", Nature Plants, vol. 1, No. 10, Sep. 28, 2015.
Ran, et al., "Genome engineering using the CRISPR-Cas9 system", Nature Protocols, Nature Publishing Group, GB, vol. 8, No. 11, pp. 2281-2308, Nov. 1, 2017.
Bikard, et al., "CRISPR Interference Can Prevent Natural Transformation and Virulence Acquisition during in Vivo Bacterial Infection", Cell Host & Microbe, Aug. 16, 2012, 177-186.
Bongjun, et al., "A Rapid and Efficient Method for Construction of an Infectious Clone of Tomato yellow leaf curl virus", The Plant Pathology Journal, 2014, 310-315.
Cong, et al., "Multiplex Genome Engineering Using CRISPR/Cas Systems", HHS Public Access, Oct. 11, 2013, 1-9.
Czosnek, et al., "Replication of tomato yellow leaf curl virus (TYLCV) DNA in agroinoculated leaf discs from selected tomato genotypes", Springer Link, Sep. 1993, 995-1005.
Doudna, et al., "The new frontier of genome engineering with CRISPR-Cas9", Science, Nov. 28, 2014, 1-11.
Elmore, et al., "Programmable plasmid interference by the CRISPR-Cas system in Thermococcus kodakarensis", RNA Biology, May 2013, 828-840.
Emerson, "Virus-Host and CRISPR Dynamics in Archaea-Dominated Hypersaline Lake Tyrrell, Victoria, Australia", Hindawi Publishing Corporation Archaea, 2013, 1-13.
Gafni, "Tomato yellow leaf curl virus, the intracellular dynamics of a plant DNA virus", Wiley Researcher Academy, Dec. 19, 2002, 1-19.
Galvez, et al., "Engineered plant virus resistance", Plant Science, 2014, 11-25.
Gasiunas, et al., "Cas9—crRNA ribonucleoprotein complex mediates specific DNA cleavage for adaptive immunity in bacteria", PNAS, Sep. 4, 2012, E2579-E2586.
Hanley-Bowdoin, et al., "Geminiviruses: masters at redirecting and reprogramming plant processes", Focus on Plant—Microbe Interaction, Nov. 2013, 777-788.
Jianbin, et al., "RNA-guided endonuclease provides a therapeutic strategy to cure latent herpesviridae infection", Cross Mark, PNAS, Sep. 9, 2014, 13157-13162.
Jinek, et al., "A Programmable Dual-RNA—Guided DNA Endonuclease in Adaptive Bacterial Immunity", Science, Aug. 17, 2012, 816-822.
Kabin, et al., "Boosting CRISPR/Cas9 multiplex editing capability with the endogenous tRNA-processing system", Cross Mark, Mar. 17, 2015, 3570-3575.

(Continued)

*Primary Examiner* — Elizabeth F McElwain
(74) *Attorney, Agent, or Firm* — Billion & Armitage; Lisbeth C. Robinson

(57) ABSTRACT

A genetically modified tobacco plant or tomato plant resistant to at least one pathogenic geminiviridae virus species is provided. The plant comprises a heterologous CRISPR/Cas9 system and at least one heterologous nucleotide sequence that is capable of hybridizing to a nucleotide sequence of the pathogenic virus and that directs inactivation of the pathogenic virus species or plurality of viral species by the CRISPR/Cas9 system. The heterologous nucleotide sequence can be complementary to, but not limited to an Intergenic Region (IR) of the Tomato Yellow Leaf Curl Virus (TYLCV). Further provided are methods of generating a genetically modified plant that is resistant to a virus pathogen by a heterologous CRISPR/Cas9 system and expression of a gRNA specifically targeting the virus.

15 Claims, 20 Drawing Sheets

Specification includes a Sequence Listing.

(56) References Cited

OTHER PUBLICATIONS

Kit-San, et al., "CRISPR/Cas9-mediated genome editing of Epstein—Barr virus in human cells", Journal of General Virology, 2015, 626-636.
Koshiro-Kimura, et al., "Construction of Plants resistant to TYLCV by using artificial zinc-finger Proteins", Oxford University Press, Sep. 27, 2009, 281-282.
Lapidot, et al., "Chapter Three—Management of Whitefly-Transmitted Viruses in Open-Field Production Systems", King Abdullah University of Science and Technology Library, 2014, 1-2.
Marraffini, et al., "CRISPR Interference Limits Horizontal Gene Transfer in Staphylococci by Targeting DNA", NIH Public Access, Jun. 12, 2009, 1843-1845.
Marraffini, et al., "CRISPR interference: RNA-directed adaptive immunity in bacteria and archaea", NIH Public Access, Apr. 13, 2011, 1-23.
Moriones, et al., "Tomato yellow leaf curl virus, an emerging virus complex causing epidemics worldwide", Virus Research, 2000, 123-134.
Prashant, et al., "RNA-Guided Human Genome Engineering via Cas9", NIH Public Access, Aug. 15, 2013, 1-8.
Pumplin, et al., "RNA silencing suppression by plant pathogens: defence, counter-defence and counter-counter-defence", Focus on Plant—Microbe Interactions, Macmillan Publishers Limited, Nov. 2013, 745-760.
Schiffer, et al., "Targeted DNA Mutagenesis for the Cure of Chronic Viral Infections", Journal of Virology, Sep. 2012, 8920-8936.
Takashi, "Inhibition of Virus DNA Replication by Artificial Zinc Finger Proteins", Journal of Virology, Feb. 2005, 2614-2619.
Tomoaki, et al., "Inhibition of Binding of Tomato Yellow Leaf Curl Virus Rep to its Replication Origin by Artificial Zinc-Finger Protein", Springer, Mol Biotechnol, 2013, 198-203.
Vanitharani, et al., "Geminiviruses and RNA silencing", Mar. 2005, 1360-1385.
Verlaan, et al., "The Tomato Yellow Leaf Curl Virus Resistance Genes Ty-1 and Ty-3 are Allelic and Code for DFDGD-Class RNA-Dependent RNA Polymerases", Plos, Mar. 2013, 1-11.
Wenhui, et al., "RNA-directed gene editing specifically eradicates latent and prevents new HIV-1 infection", Cross-Mark, PNAS Early Edition, Jun. 19, 2014, 1-6.
Yang, et al., "Use of Tomato yellow leaf curl virus (TYLCV) Rep Gene Sequences to Engineer TYLCV Resistance in Tomato", Phytopathology, Jan. 19, 2004, 490-496.
Zahir, et al., "Efficient Virus-Mediated Genome Editing in Plants Using the CRISPR/Cas9 System", Cell Press Partner Journal, Molecular Plant letter to the Editor, 2015, 1288-1291.
Zhen, et al. "Harnessing the clustered regularly interspaced short palindromic repeat (CRISPR)/CRISPR-associated Cas9 system to disrupt the hepatitis B virus", Gene Therapy, 2015, 404-412.

\* cited by examiner

IR-gRNA: GGCCATCCGTATAATATTAC
CP-gRNA: CTTCGGCGAACCTTCGAGAC
RCRII-gRNA: TGGATGAGCACATGCAAGTG

```
              SspI         PAM
WT   CGCTCCAAAAAGCGGGCCATCCGTATAATATTACCGGATGGCCGCGAATTTT
G04  CGCTCC------------------------TACCGGATGGCCGCGAATTTT   -24
G06  CGCTCCAAAAAGC-----------------TACCGGATGGCCGCGAATTTT   -17
D02  CGCTCCAAAAAGCGGGCCATCCGTATAATA---------GGCCGCGAATTTT  -09
H09  CGCTCCAAAAAGCGGGCCATCCGTATA---TTACCGGATGGCCGCGAATTTT   -03
C02  CGCTCCAAAAAGCGGGCCATCCGTATAATATATTACCGGATGGCCGCGAATTTT +2
F04  CGCTCCAAAAAGCGGGCCATCCGTATAATAGTTACCGGATGGCCGCGAATTTT  T>G
```

Fig. 2D

```
                                       PAM
WT   TTTTTGCACTGGGAACTTTTCCTTCCGAACTGGATGAGCACAATGCAAGTGAGGAG
F11  TTTTTGCACTGGGAACTTTTCCTTCCGAACTGGATGAGCACATG--AGTGAGGAG   -02
C02  TTTTTGCACTGGGAACTTTTCCTTCCGAACTGGATGAGCACA----GTGAGGAG    -05
A08  TTTTTGCACTGGGAACTTTTCCTTCCGAACT--------------AGTGAGGAG    -15
B07  T-----------------------------------------AGTGAGGAG      -42
H02  TTTTTGCACTGGGAACTTTTCCTTCCGAACTGGATGAGCACAATGCAAAGTGAGGAG +A
```

TYLCV  GGCCATCCGTATAATATTAC
Worland  GCCATCCGCA₂TAATATTAC

*Fig. 3A*

```
     TYLCV  +  +  +  +  +  -  -  -
       TRV  -  +  -  -  -  -  -  -
IRgRNA-TYLCV +  +  +  +  +  +  +  +
   WORLAND  -  -  -  -  -  +  +  +
```

*Fig. 3B*

```
                SspI      PAM
                          ***
WT  ATCATCACGCTCCAAAAAGCGGCCATCCGTATAATATTACCGGATGGCCGCGGAATTTTGTGTGGGCCC
C09 ATCATCACGCTCCAAAAAGCGGCCATCCGTATAATATTA-----------------GTGTGGGCCC  -19
D02 ATCATCACGCTCCAAAAAGCGGCCATCCGTATAATATTA-------GGCCGGAATTTTGTGTGGGCCC  -09
B01 ATCATCACGCTCCAAAAAGCGGCCAT-----------TACCGGATGGCCGCGGAATTTTGTGTGGGCCC  -11
A03 ATCATCACGCTCCAAAAAGCGGCCATCCGTATAATCTTACCGGATGGCCGCGGAATTTTGTGTGGGCCC  T>C
F04 ATCATCACGCTCCAAAAAGCGGCCATCCGTAATAGTACCGGATGGCCGCGGAATTTTGTGTGGGCCC   T>G

SspI      PAM
                          ***
WT  GCCCTTATATACCTCCAGGGGCCCATCCGCAATAATAATTATTACCGGATGGCCCCGAAAATTTTGCCCCCCCA
B02 GCCCTTATATACCTCCAGGGGC--TCCGCAATAATAATTATTACCGGATGGCCCCGAAAATTTTGCCCCCCCA  -2
G01 GCCCTTATATACCTCCAGGGGA--CATCCGCAATAATAATTATTACCGGATGGCCCCGAAAAATTTTGCCCCCCCA +01/-02
H02 GCCCTTATATACCTCCAGGGGT--CATCCGCAATAATAATTATTACCGGATGGCCCCGAAAAATTTTGCCCCCCCA +01/-02
G03 GCCCTTATATACCTCCAGGGGC--ATCCGCAATAATAATTATTACCGGATGGCCCCGAAAATTTTGCCCCCCCA   -1
H03 GCCCTTATATACCTCCAGGGGC--ATCCGCAATAATAGTATTACCGGATGGCCCCGAAAATTTTGCCCCCCCA    -1
```

*Fig. 3C*

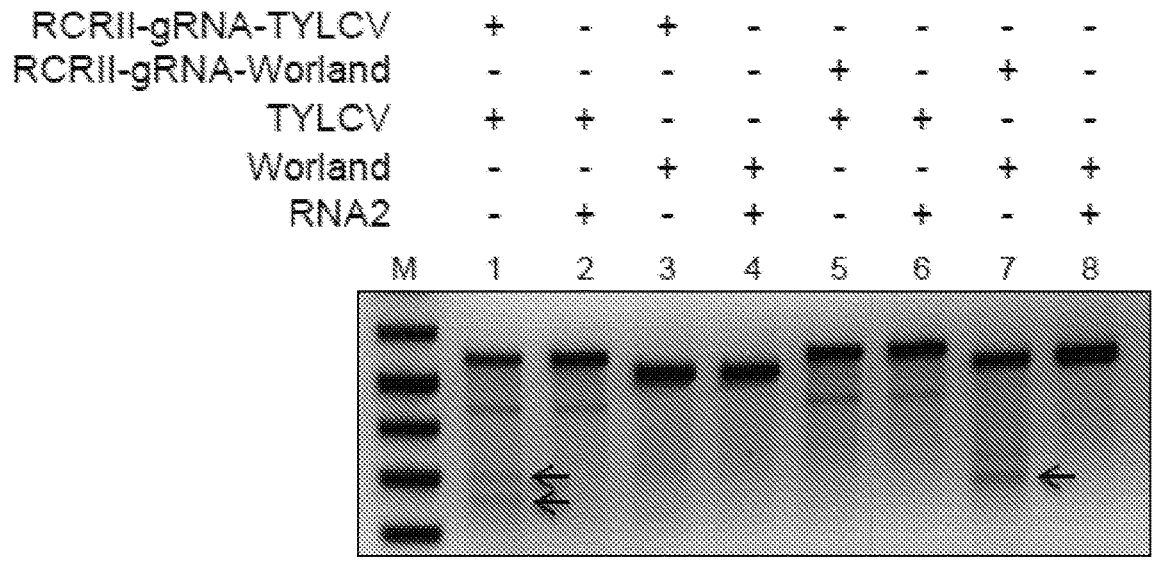

|                  | 1 | 2 | 3 | 4 | 5 | 6 | 7 | 8 |
|---|---|---|---|---|---|---|---|---|
| RCRII-gRNA-TYLCV | + | − | + | − | − | − | − | − |
| RCRII-gRNA-Worland | − | − | − | − | + | − | + | − |
| TYLCV | + | + | − | − | + | + | − | − |
| Worland | − | − | + | + | − | − | + | + |
| RNA2 | − | + | − | + | − | + | − | + |

Fig. 4A

```
                                      PAM
WT    TCCTTCGAACTGGATGAGCACATGCAAGTGAGGAGTCCCATCTT
B03   TCCTTCGAACTGGATGAG--------------GAGTCCCATCTT   -14
E09   TCCTTCGAACTGGATGAGCACAGG-----GAGGAGTCCCATCTT   +2/-7
D03   TCCTTCGAACTGGATGAGCACA-----GTGAGGAGTCCCATCTT   -5
F08   TCCTTCGAACTGGATGACCACATGCAAGTGAGGAGTCCCATCTT   G>C
      TCCTTCGAACTGGATGAGCCCATCCAAGTGAGGAGTCCCATCTT   A>C/G>C
```

Fig. 4B

```
                                      PAM
WT    TGTGCTTTAC CTTTGAATTGGATGAGGGCGTGGAGATGCAGAGAC
A03   TGTGCTTTACCTTTGAATTGG------GCGTGGAGATGCAGAGAC   -06
C06   TGTGCTTTACCTTTGAATTGGATGAGG---TGGAGATGCAGAGAC   -03
C08   TGTGCTTTACCTTTGAATTGGATGAGG-CGTGGAGATGCAGAGAC   -01
A06   TGTGCTTTACCTTTGAATTGGATGAGGGCGTGGAGATGCAGAGAC   +01
G02   TGTGCTTTACCTTTGAATTGGATGAGGAGCGTGGAGATGCAGAGAC  +01
```

Fig. 4C

SEQ ID NO: 101
GGCCATCCGTATAATATTACCGGATGGCCGCGAATTTTGTGTGGGCCCCTCAACGCACTAA
CTGACAAGGACATGCGAACCAATCAAATTGCATCCTCAAACGTTAGATAAGTGTTCATTTG
TcTTTATATACTTGGTCCCCAAGTATTTTGTCTTGCAATATGTGGGACCCACTTCTAAATG
AATTTCCTGAATCTGTTCACGGATTTCGTTGTATGTTAGCTATTAAATATTTGCAGGCTGT
TGAGGAAACTTACGAGCCCAATACATTGGGCCACGATTTAATTAGGGATCTTATATCTGTT
GTAAGGGCCCGTGACTATGTCGAAGCGACCAGGCGATATAATCATTTCCACGCCCGTCTCG
AAGGTTCGCCGAAGGCTGAACTTCGACAGCCCATACAGCAGCCGTGCTGCTGTCCCCATTG
TCCAAGGCACAAACAAGCGACGATCATGGACGTACAGGCCCATGTACCGAAAGCCCAGAAT
ATACAGAATGTATCGAAGCCCTGATGTTCCCGTGGATGTGAAGGCCCATGTAAAGTCCAG
TCTTATGAGCAACGGGATGATATTAAGCATACTGGTATTGTTCGTTGTGTTAGTGATGTTA
CTCGTGGATCTGGAATTACTCACAGAGTGGGTAAGAGGTTCTGTGTTAAATCGATATATTT
TTTAGGTAAAGTCTGGATGGATGAAAATATCAAGAAGCAGAATCACACTAATCAGGTCATG
TTCTTCTTGGTCCGTGATAGAAGGCCTTATGGAAGCAGCCCAATGGATTTTGGACAGGTTT
TTAATATGTTCGATAATGAGCCCAGTACCGCAACCGTGAAGAATGATTTGCGGGATAGGTT
TCAAGTGATAAGGAAATTTCATGCTACAGTTATTGGTGGGCCCTCTGGAATGAAGGAACAG
GCATTAGTTAAGAGATTTTTTAGAATTAACAGTCATGTAACTTATAATCATCAGGAGGCAG
CCAAGTATGAGAACCATACTGAGAACGCCTTGTTATTGTATATGGCATGTACGCATGCCTC
TAATCCAGTGTATGCAACTATGAAAATACGCATCTATTTCTATGATTCAATATCAAATTAA
TAAATTTTATATTTTATATCATGACTTTCTGTTACATTTATTGTGTTTTCAAGTACATCAT
ACAATACATGATCAACTGCTCTGATTACATTGTTAATGGAAATTACACCAAGACTATCTAA
ATACTTAAGAACTTGATATCTAAATACTCTTAAGAAACGACCAGTCTGAGGCCGTAAGGTC
GTCCAGATTTGGAAGTTGAGATAACATTTGTGAATCCCCAGTACCTTCCTGATATTGTGAT
TGAATCTTATCTGTATTGAAATGATGTCGTGGCTCATTAGAAATGGCCTCTCGTCGTGGTT
GGTGATCTTGAAATATAGGGGATTTTCTATCTCCCATATAAAACGCCATTCTGGGCTTGA
TGAGCAGTGATGAGTTCCCCGGTGCGTGAATCCATGATTGATGCAGTTGATGTGGAGGTAA
TATGAGCATCCGCAGTCGAGGTCTATGCGCTTACGTCTGACTGGCTTAGTCTTCGCTATGC
GGTGTTGGATTTTGATTGGCACTTGAGAACAGTGGCTCGTAGAGGGTGACGAAGGTTGCAT
TCTTGAGAGCCCAATTTTTCAAGGATATGTTTTTTTCTTCGTCTAGATATTCCCTATATGA
TGAGGTAGGTCCTGGATTGCAGAGGAAGATAGTGGGAATTCCCCCTTTAATTTGAATCGGC
TTCCCGTACTTTGTGTTGCTTTGCCAGTCCCTCTGGGCCCCATGAATTCCTTGAAGTGCT
TTAAATAATGCGGGTctacgtcatcgatgacgttgtaccacgcatcattactgtacacctt
tggacttaggtctagatgtccacataaataattatgtgggcctagagacctggcccacatt
gtcttccccgttctgctatcaccctcgatgacaatactattaggtctCCATGGCCGCGCAG
CGGAAGACATGACGTTCTCGGACACCCATACTTCAAGTTCATCTGGAACTTGATTAAAAGA
TGAAGATAAAAAGGGAGAAATATAAGGAGCCGGAGGCTCCTGAAAAATTCTATCTAAATTT
GAATTTAAATTATGAAATTGAAGTATAAAGTCTCTAGGAGCTTTCTCCTTCAGTATATTGA
GGGCCTGAGCTTTGGACCCTGAATTGATTGCCTCGGCATATGCGTCGTTGGCAGATTGGCA
ACCTCCTCTAGCTGATCGTCCATCGACTTGGAAAACTCCATGATCAATGACGTCTCCGTCT
TTTTCCATATAGGATTTGACATCGCTTGAACTCTTAGCTCCCTGAATGTTCGGATGGAAAT
GTGCTGACCTGGTTGGGATGTGAGGTCGAAGAATCTGTTGTTTTGCACTGGAACTTTCC
TTCGAACTGGATGAGCACATGCAAGTGAGGAGTCCCATCTTCATGAAGCTCTCTGCAGATT
CTAATGAATTTTTTGGAAGTGGGTGTTTGTATATTTAATAATTGGGAAAGTGCTTCCTCTT
TAGTTAGAGAGCATTTGGGATAAGTGAGAAAATAATTTTTGGCATTTATTTTAAACCGATT
GGGGGCTGCCATATTGACTTGGTCAATCGGAGTCTCTCAACTCTTTCTATGTATTGGTGTA
TTGGAGTCCTATATATATGGAGACTCCAATGGCATATATGTAAATATTGTACTTTAATTCA
AAATCATCACGCTCCAAAAAGC

*Fig. 6*

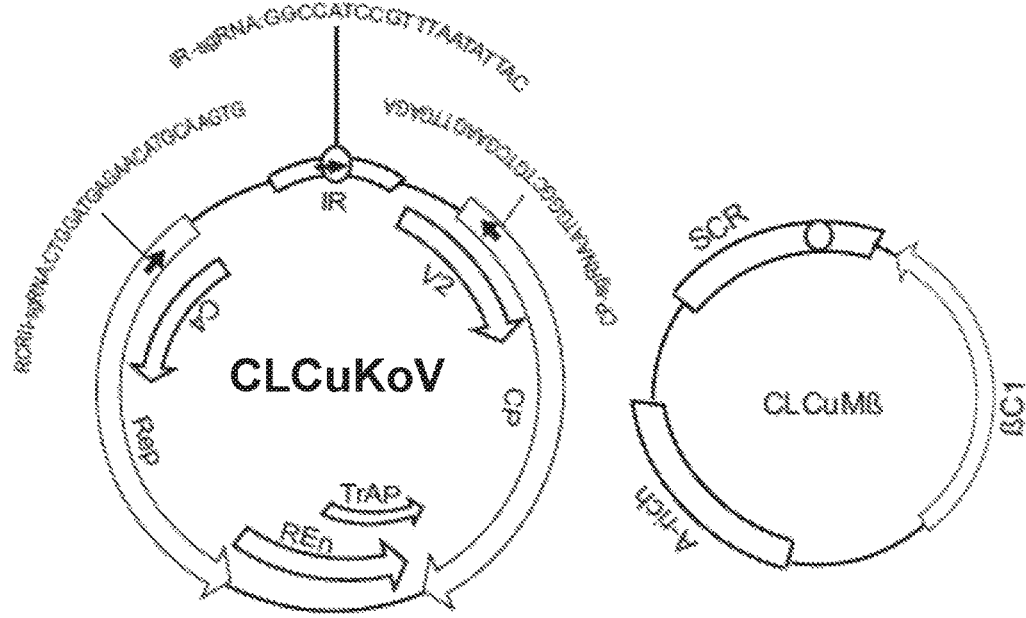
*Fig. 7A*
| CLCuKoV-CPsgRNA | + | + | + | − | − |
| RNA1 | + | + | + | + | − |
| RNA2 | − | − | − | + | − |
| CLCuKoV | + | + | + | + | + |
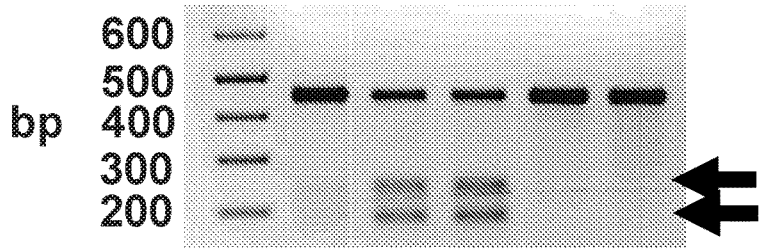
Indels %   24  49  65  0  0
*Fig. 7B*
```
              PAM
WT   AAGGTACGCCGCCG[TCTCAACTTCGACAGCCCAT]A
B06  AAGGTACG-------------CAACTTCGACAGCCCATA  -9
C03  AAGGTACGCCGCCGTCT------TCGACAGCCCATA     -5
A11  AAGGTACGCCGCCGTCTCTTCG---ACAGCCCATA      -3
A10  AAGGTACGCCGCCGTCTTCAACTTCGACAGCCCAT      C>T
E03  AAGGTACGCCGCCGTCTGCAACTTCGACAGCCCAT      C>G
```
*Fig. 7C*

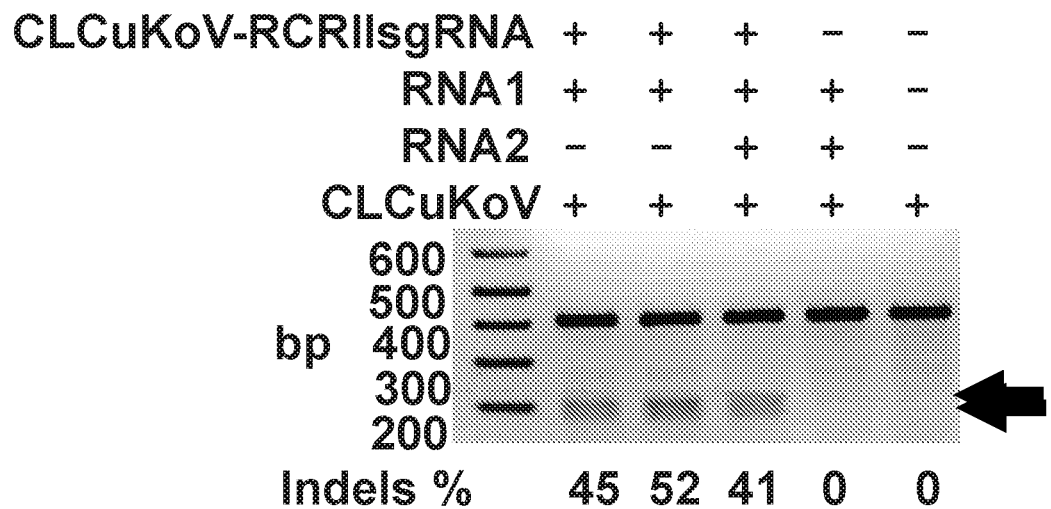
*Fig. 7D*
```
                                    PAM
WT  CCCTTCGAA CTGGATGAGAACATGCAAGTG AGGAG
E08 CC------------------------------AGTGAGGAG  -24
G01 CCCTTCGAACT---------------------AGTGAGGAG  -15
A01 CCCTTCGAACTGGATGAGAACA----------AGTGAGGAG  -4
G02 CCCTTCGAACTGGATGAGAACATGCAAAGTGAGGA         G>A
```
*Fig. 7E*
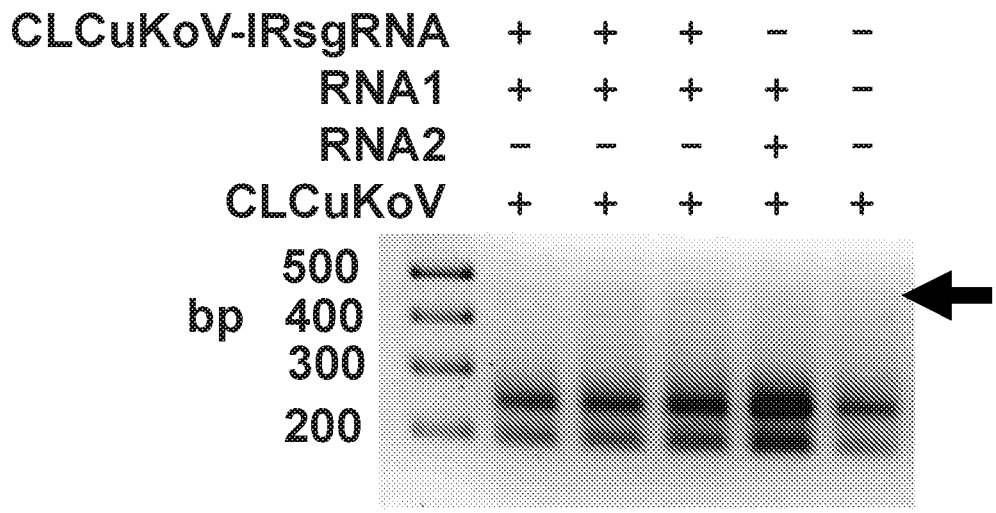
*Fig. 7F*

| MeMV-IRsgRNA | + | + | + | − |
| RNA1 | + | + | + | + |
| MeV | + | + | + | + |

```
             bp  500
                 400  ←
                 300
                 200
                 100
```

Indels %         0    13   19   17

*Fig. 8A*

```
                                    SspI           PAM
WT    TTTGCAACACGTGGCC GCCATCCGCTATAATATTAC CGGATGGC
B09   TTTGCAACACGTGGCGGCCA-------------------GATGGC  -18
H12   TTTGCAACACGTGGCGGCCATCCG---------------GATGGC  -14
G01   TTTGCAACACGTGGCGGCCATCCCGCTATAATATTACCGGATGAC  mic
E02   TTTGCAACACGTGGCGGCCATCCGCTATAATATTACCGGATGACC  G>A
```

*Fig. 8B*

| MeMV-CPsgRNA | − | − | + | + | + |
| RNA1 | − | + | + | + | + |
| RNA2 | − | + | − | − | − |
| MeV | + | + | + | + | + |

```
      500
      400
bp    300                               ←
      200
      100                               ←
```

Indels %   0    0    21   26   31

*Fig. 8C*

```
                                                    PAM
WT   TTTCTCGCC ACGTGGAGGTATGGGCCCTA GGCCGCTGC
D02  TTTCTCGCCACGTGGAGGTA------CTAAGGCCGCTGC    -6
A06  TTTCTCGCCACGTGGAGGTA-----CCTAAGGCCGCTGC    -5
A12  TTTCTCGCCACGTGGAGGTATGGG-CCTAAGGCCGCTGC    -1
G02  TTTCTCGCCACGTGAAGGTATGGGCCCTAATGCCGCTGC    G>A,G>T
```

*Fig. 8D*

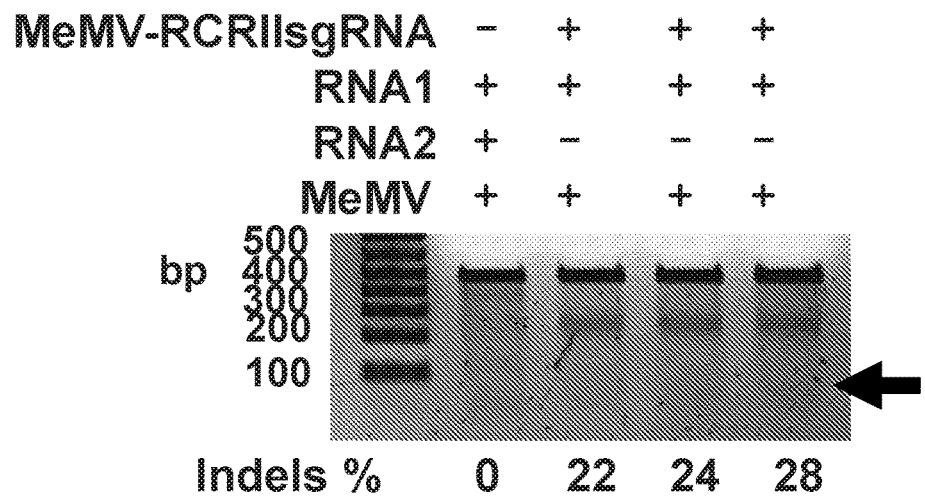

*Fig. 8E*

```
                                                      PAM
WT   TTTTCCTTCGAA CTGGATAAGCACATGGAGATG AGGTTC
B01  TTTTCCTTCGAACTGGATA---------------GATGAGGTTC   -10
C03  TTTTCCTTCGAACTGGATAAGCACATG---ATGAGGTTC        -3
G07  TTTTCCTTCGAACTGGATAAGCACATGGA--TGAGGTTC        -2
B11  TTTTCCTTCGAACTGGATAAGCACATGGAGGATGAGGTTC       +1
```

*Fig. 8F*

TYLCSV-IRsgRNA  + + + − −
RNA1            + + + + −
RNA2            − − − + −
TYLCSV          + + + + +

TYLCV2.3-IRsgRNA − − + + + −
TYLCV-IRsgRNA    + + − − − −
RNA1             + + + + + +
RNA2             − − − − − +
TLYCV2.3         + + + + + +

Indels %          21 17 45 37 41 0

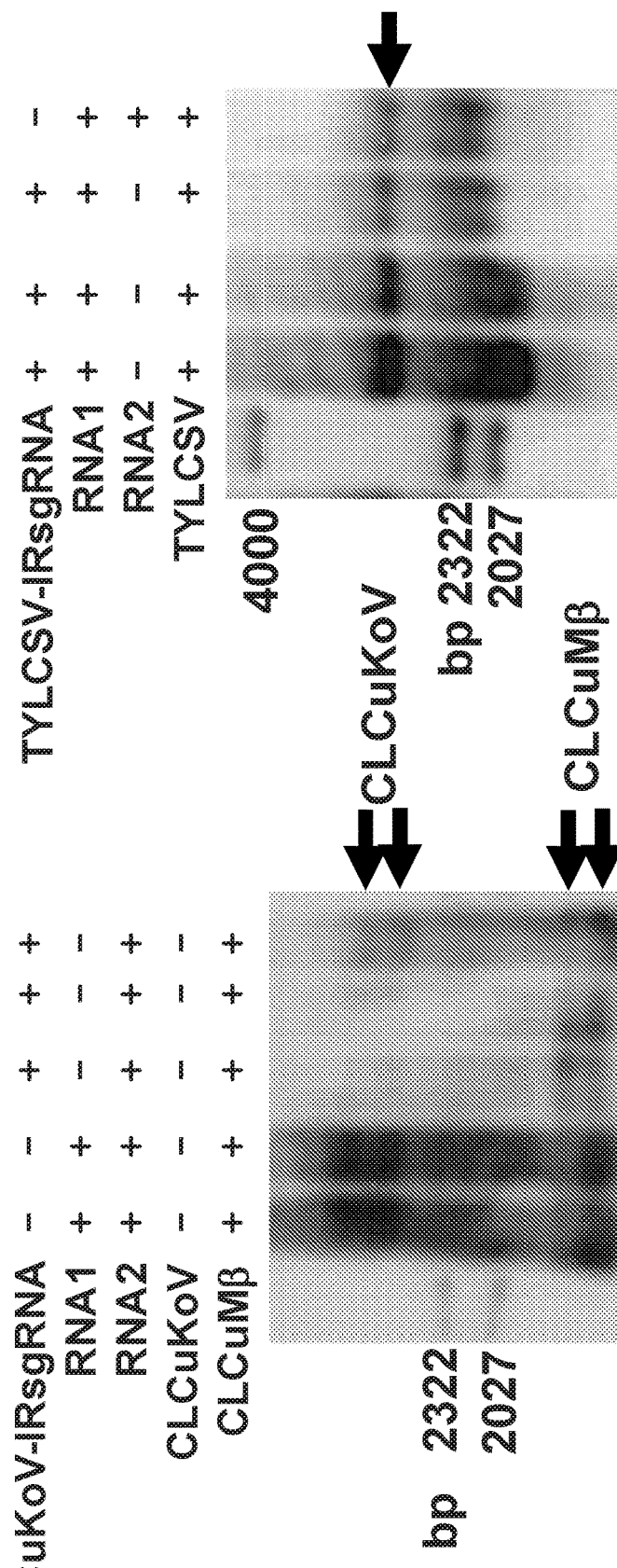

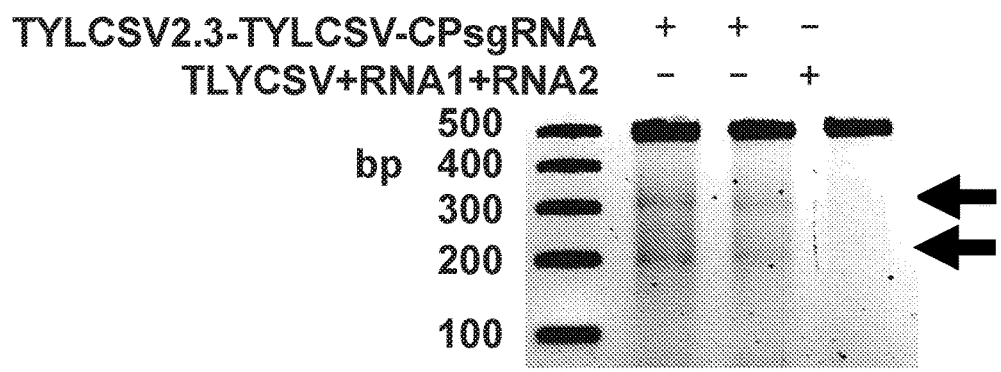
Fig. 11C
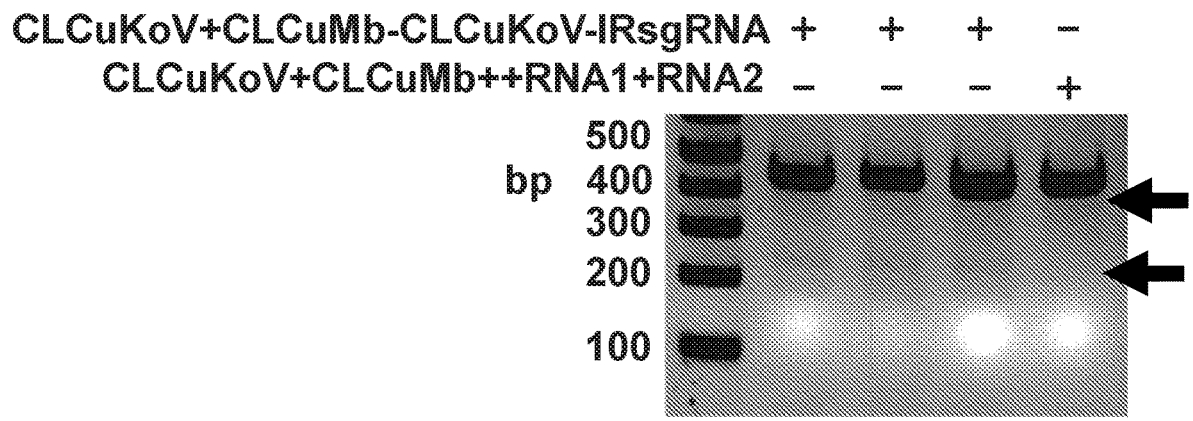
Fig. 11D
Fig. 11E

SEQUENCE LISTING

```
<160> NUMBER OF SEQ ID NOS: 119

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 1
aaggtacgcc gccgtctcaa cttcgacagc ccata                              35

<210> SEQ ID NO 2
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: B06 WT -9

<400> SEQUENCE: 2
aaggtacgca acttcgacag cccata                                          26

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C03 WT -5

<400> SEQUENCE: 3
aaggtacgcc gccgtcttcg acagcccata                                      30

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A11 WT -3

<400> SEQUENCE: 4
aaggtacgcc gccgtctctt cgacagccca ta                                   32

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A10 WT C to T

<400> SEQUENCE: 5
aaggtacgcc gccgtcttca acttcgacag cccat                                35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E03 WT C to G

<400> SEQUENCE: 6
aaggtacgcc gccgtctgca acttcgacag cccat                                35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT
```

```
<400> SEQUENCE: 7
cccttcgaac tggatgagaa catgcaagtg aggag                              35

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E08 WT -24

<400> SEQUENCE: 8
ccagtgagga g                                                       11

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G01 WT -15

<400> SEQUENCE: 9
cccttcgaac tagtgaggag                                              20

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A01 WT -4

<400> SEQUENCE: 10
cccttcgaac tggatgagaa caagtgagga g                                 31

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G02 WT G to A

<400> SEQUENCE: 11
cccttcgaac tggatgagaa catgcaaagt gagga                             35

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 12
tttgcaacac gtggcggcca tccgctataa tattaccgga tggc                   44
```

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: B09 WT -18

<400> SEQUENCE: 13
tttgcaacac gtggcggcca gatggc                                                26

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: H12 WT -14

<400> SEQUENCE: 14
tttgcaacac gtggcggcca tccggatggc                                            30

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: G01 WT mic

<400> SEQUENCE: 15
tttgcaacac gtggcggcca tcccgctata atattaccgg atgac                           45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: E02 WT G to A

<400> SEQUENCE: 16
tttgcaacac gtggcggcca tccgctataa tattaccgga tgacc                           45

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: WT

<400> SEQUENCE: 17
tttctcgcca cgtggaggta tgggccctaa ggccgctgc                                  39

<210> SEQ ID NO 18
<211> LENGTH: 33

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: D02 WT -6

<400> SEQUENCE: 18
tttctcgcca cgtggaggta ctaaggccgc tgc                33

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A06 WT -5

<400> SEQUENCE: 19
tttctcgcca cgtggaggta cctaaggccg ctgc               34

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: A12 WT -1

<400> SEQUENCE: 20
tttctcgcca cgtggaggta tgggcctaag gccgctgc            38

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: G02 WT G to A, G to T

<400> SEQUENCE: 21
tttctcgcca cgtgaaggta tgggccctaa tgccgctgc           39

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: WT

<400> SEQUENCE: 22
ttttccttcg aactggataa gcacatggag atgaggttc           39

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic -continued

```
      oligonucleotide
<220> FEATURE:
<223> OTHER INFORMATION: B01 WT -10

<400> SEQUENCE: 23 tttccttcg aactggatag atgaggttc                                    29

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C03 WT -3

<400> SEQUENCE: 24
ttttccttcg aactggataa gcacatgatg aggttc                           36

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G07 WT -2

<400> SEQUENCE: 25
ttttccttcg aactggataa gcacatggat gaggttc                          37

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: B11 WT

<400> SEQUENCE: 26
ttttccttcg aactggataa gcacatggag gatgaggttc                       40

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TYLCV2.3

<400> SEQUENCE: 27
gcggccatcc gtataatatt accggatggc cgc                              33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TYLCSV
```

<400> SEQUENCE: 28
gcggccatcc gtttaatatt accggatggc cgc                                33

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MeMV-A

<400> SEQUENCE: 29
gcggccatcc gctataatat taccggatgg ccgc                               34

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: MeMV-B

<400> SEQUENCE: 30
gcggccatcc gctataatat taccggatgg ccgc                               34

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CLCuKV

<400> SEQUENCE: 31
gcggccatcc gtttaatatt accggatggc cgc                                33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CLCuMBeta

<400> SEQUENCE: 32
gcggccatcc gtttaatatt accggatggc cgc                                33

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 33
taataattgg gaaagtgctt tcacggtttt aggtgtatgt                         40

```
<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C05

<400> SEQUENCE: 34
taataattgg gaaagtgctt tcacggtttt aggtgtatgt                              40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E08

<400> SEQUENCE: 35
taataattgg gaaagtgctt tcacggtttt aggtgtatgt                              40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E11

<400> SEQUENCE: 36
taataattgg gaaagtgctt tcacggtttt aggtgtatgt                              40

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 37
ttcagccttc ggcgaacctt cgaggcgggc gtggaaa                                 37

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C03

<400> SEQUENCE: 38
ttcagccttc ggcgaacctt cgagacgggc gtggaaa                                 37

<210> SEQ ID NO 39
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E06

<400> SEQUENCE: 39
ttcagccttc cgcgaacctt cgagatgggc gtggaaa                              37

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F12

<400> SEQUENCE: 40
ttcagccttc ggcgaacctt ctagacgggc gtggaaa                              37

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G06

<400> SEQUENCE: 41
ttcagccttc ggcgaacctt ctagacgggc gtgggaa                              37

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D12

<400> SEQUENCE: 42
ttcagccttc ggcgaacctt ctaggcggga gtggaaa                              37

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV2.3-IR-T-F

<400> SEQUENCE: 43
aattgggaaa gtgcttcctc t                                               21

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Primer TYLCV2.3-IR-T-R

<400> SEQUENCE: 44
atagtcacgg gcccttacaa ca                                              22

<210> SEQ ID NO 45
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV-IR-T1

<400> SEQUENCE: 45
cgagtctaga ggccatccgt ataatattac gttttagagc tagaaatagc aag            53

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer SPDK-gRNA-R

<400> SEQUENCE: 46
acatgcccgg gaaaaaaagc accgactcgg                                      30

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-ACTIN1-RT-F

<400> SEQUENCE: 47
tgaagatcct cacagagcgt gg                                              22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-ACTIN1QRT-LIU-R

<400> SEQUENCE: 48
ttgtatgtgg tctcgtggat tc                                              22

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV-CP-T1

<400> SEQUENCE: 49
```
cgagtctaga gcttcggcga accttcgaga cgttttagag ctagaaatag caag         54

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV-RCRIII-T1

<400> SEQUENCE: 50
cgagtctaga gaagcgatgt caaatcctat agttttagag ctagaaatag caag         54

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV1-RELICASE-RT-F

<400> SEQUENCE: 51
ctactgggag agcagcaacc                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV1-REPLICASE-RT-R

<400> SEQUENCE: 52
ctgagcgcaa aagtacacca                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV2-CP-RT-F

<400> SEQUENCE: 53
ttgggtggaa tcagtttcgt                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV2-CP-RT-R

<400> SEQUENCE: 54
tcttccaaag tcgagccagt                                              20

```
<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer WOR-L1-T1/2-F

<400> SEQUENCE: 55
tgcttcagct gcattacctg                                                     20

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer WOR-L1-T1/2-R

<400> SEQUENCE: 56
atggccsctg gaggtatata ag                                                  22

<210> SEQ ID NO 57
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer WOR-RCRII-T

<400> SEQUENCE: 57
cgagtctaga gctttgaatt ggatgagggc ggttttagag ctagaaatag caag              54

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV 2.3-CP-T1/2-F

<400> SEQUENCE: 58
ttcttcacgg ttgcggtact                                                     20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV2.3-CP-T1/2-R

<400> SEQUENCE: 59
gagctttgga ccctgaattg                                                     20

<210> SEQ ID NO 60
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Primer TYLCV2.3-REP-T1/2-F

<400> SEQUENCE: 60
gagctttgga ccctgaattg                                               20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TYLCV2.3-REP-T1/2-R

<400> SEQUENCE: 61
ttggagcgtg atgattttga                                               20

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 62
cgctccaaaa agcggccatc cgtataatat taccggatgg ccgcgaattt              50

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G04 WT -24

<400> SEQUENCE: 63
cgctcctacc ggatggccgc gaattt                                        26

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G06 WT -17

<400> SEQUENCE: 64
cgctccaaaa agctaccgga tggccgcgaa ttt                                33

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: D02 WT -09

<400> SEQUENCE: 65
cgctccaaaa agcggccatc cgtataatag gccgcgaatt t          41

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: H09 WT -03

<400> SEQUENCE: 66
cgctccaaaa agcggccatc cgtatattac cggatggccg cgaattt          47

<210> SEQ ID NO 67
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C02 WT

<400> SEQUENCE: 67
cgctccaaaa agcggccatc cgtataatat attaccggat ggccgcgaat tt          52

<210> SEQ ID NO 68
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F04 T to G

<400> SEQUENCE: 68
cgctccaaaa agcggccatc cgtataatag taccggatgg ccgcgaattt          50

<210> SEQ ID NO 69
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 69
tttttgcact ggaactttcc ttcgaactgg atgagcacat gcaagtgagg ag          52

<210> SEQ ID NO 70
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F11 WT -02

<400> SEQUENCE: 70

```
tttttgcact ggaactttcc ttcgaactgg atgagcacat gagtgaggag        50

<210> SEQ ID NO 71
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C02 WT -05

<400> SEQUENCE: 71
tttttgcact ggaactttcc ttcgaactgg atgagcacag tgaggag           47

<210> SEQ ID NO 72
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A08 WT -15

<400> SEQUENCE: 72
tttttgcact ggaactttcc ttcgaactag tgaggag                      37

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: B07 WT -42

<400> SEQUENCE: 73
tagtgaggag                                                    10

<210> SEQ ID NO 74
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: H02 WT

<400> SEQUENCE: 74
tttttgcact ggaactttcc ttcgaactgg atgagcacat gcaaagtgag gag    53

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TYLCV

<400> SEQUENCE: 75
ggccatccgt ataatattac                                         20

<210> SEQ ID NO 76
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Worland

<400> SEQUENCE: 76
gccatccgca ataatattac                                                   20

<210> SEQ ID NO 77
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 77
atcatcacgc tccaaaaagc ggccatccgt ataatattac cggatggccg cgaattttgt       60
gtgggccc                                                                68

<210> SEQ ID NO 78
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C09 WT -19

<400> SEQUENCE: 78
atcatcacgc tccaaaaagc ggccatccgt ataatattag tgtgggccc                   49

<210> SEQ ID NO 79
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D02 WT -09

<400> SEQUENCE: 79
atcatcacgc tccaaaaagc ggccatccgt ataataggcc gcgaattttg tgtgggccc        59

<210> SEQ ID NO 80
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E01 WT -11

<400> SEQUENCE: 80
atcatcacgc tccaaaaagc ggccattacc ggatggccgc gaattttgtg tgggccc          57

<210> SEQ ID NO 81
<211> LENGTH: 68
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: A03 WT T to C

<400> SEQUENCE: 81
atcatcacgc tccaaaaagc ggccatccgt ataatcttac cggatggccg cgaattttgt    60
gtgggccc                                                             68

<210> SEQ ID NO 82
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: F04 WT T to G

<400> SEQUENCE: 82
atcatcacgc tccaaaaagc ggccatccgt ataatagtac cggatggccg cgaattttgt    60
gtgggccc                                                             68

<210> SEQ ID NO 83
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: WT

<400> SEQUENCE: 83
gcccttatat acctccaggg gccatccgca ataatattac cggatggccc cgaaaatttt    60
gcccccca                                                             69

<210> SEQ ID NO 84
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: B02 WT -02

<400> SEQUENCE: 84
gcccttatat acctccaggg gctccgcaat aatattaccg gatggcsccg aaaatttgc    60 ccccca                                                               67

<210> SEQ ID NO 85
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: G01 WT +01 / -02

<400> SEQUENCE: 85
gcccttatat acctccaggg acatccgcaa taatattacc ggatggcccc gaaaatttg    60 cccccca                                                              68

<210> SEQ ID NO 86
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: H02 WT +01 / -02

<400> SEQUENCE: 86
gcccttatat acctccaggg tcatccgcaa taatattacc ggatggcccc gaaaattttg      60
cccccca                                                              68

<210> SEQ ID NO 87
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G03 WT -01

<400> SEQUENCE: 87
gcccttatat acctccaggg gcatccgcaa taatattacc ggatggcccc gaaaattttg      60
cccccca                                                              68

<210> SEQ ID NO 88
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: H03 WT -01

<400> SEQUENCE: 88
gcccttatat acctccaggg gcatccgcaa taatattacc ggatggcccc gaaaattttg      60
cccccca                                                              68

<210> SEQ ID NO 89
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 89
tccttcgaac tggatgagca catgcaagtg aggagtccca tctt                      44

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: B03 WT

<400> SEQUENCE: 90
tccttcgaac tggatgagga gtcccatctt                                    30

<210> SEQ ID NO 91
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: E09 WT 7

<400> SEQUENCE: 91
tccttcgaac tggatgagca cagggaggag tcccatctt                          39

<210> SEQ ID NO 92
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D03 WT -5

<400> SEQUENCE: 92
tccttcgaac tggatgagca cagtgaggag tcccatctt                          39

<210> SEQ ID NO 93
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F08 WT G to C

<400> SEQUENCE: 93
tccttcgaac tggatgacca catgcaagtg aggagtccca tctt                    44

<210> SEQ ID NO 94
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT A to C / G to C

<400> SEQUENCE: 94
tccttcgaac tggatgagcc catccaagtg aggagtccca tctt                    44

<210> SEQ ID NO 95
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: WT

<400> SEQUENCE: 95
tgtgctttac ctttgaattg gatgagggcg tggagatgca gagac                   45

<210> SEQ ID NO 96
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A03 WT -06

<400> SEQUENCE: 96
tgtgctttac ctttgaattg ggcgtggaga tgcagagac                39

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C06 WT -03

<400> SEQUENCE: 97
tgtgctttac ctttgaattg gatgaggtgg agatgcagag ac             42

<210> SEQ ID NO 98
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: C08 WT -01

<400> SEQUENCE: 98
tgtgctttac ctttgaattg gatgaggcgt ggagatgcag agac           44

<210> SEQ ID NO 99
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: A06 WT

<400> SEQUENCE: 99
tgtgctttac ctttgaattg gatgaggggc gtggagatgc agagac         46

<210> SEQ ID NO 100
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: G02 WT

<400> SEQUENCE: 100
tgtgctttac ctttgaattg gatgaggagc gtggagatgc agagac         46

<210> SEQ ID NO 101
<211> LENGTH: 2767
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TYLCV 2.3 genome

<400> SEQUENCE: 101

```
ggccatccgt ataatattac cggatggccg cgaattttgt gtgggcccct caacgcacta      60
actgacaagg acatgcgaac caatcaaatt gcatcctcaa acgttagata agtgttcatt     120
tgtctttata tacttggtcc ccaagtattt tgtcttgcaa tatgtgggac ccacttctaa     180
atgaatttcc tgaatctgtt cacggatttc gttgtatgtt agctattaaa tatttgcagg     240
ctgttgagga aacttacgag cccaatacat tgggccacga tttaattagg gatcttatat     300
ctgttgtaag ggcccgtgac tatgtcgaag cgaccaggcg atataatcat ttccacgccc     360
gtctcgaagg ttcgccgaag gctgaacttc gacagcccat acagcagccg tgctgctgtc     420
cccattgtcc aaggcacaaa caagcgacga tcatggacgt acaggcccat gtaccgaaag     480
cccagaatat acagaatgta tcgaagccct gatgttcccc gtggatgtga aggcccatgt     540
aaagtccagt cttatgagca acgggatgat attaagcata ctggtattgt tcgttgtgtt     600
agtgatgtta ctcgtggatc tggaattact cacagagtgg gtaagaggtt ctgtgttaaa     660
tcgatatatt ttttaggtaa agtctggatg atgaaaata tcaagaagca gaatcacact     720
aatcaggtca tgttcttctt ggtccgtgat agaaggcctt atggaagcag cccaatggat     780
tttggacagg ttttttaatat gttcgataat gagcccagta ccgcaaccgt gaagaatgat     840
ttgcgggata ggtttcaagt gataaggaaa tttcatgcta cagttattgg tgggccctct     900
ggaatgaagg aacaggcatt agttaagaga ttttttagaa ttaacagtca tgtaacttat     960
aatcatcagg aggcagccaa gtatgagaac catactgaga acgccttgtt attgtatatg    1020
gcatgtacgc atgcctctaa tccagtgtat gcaactatga aaatacgcat ctatttctat    1080
gattcaatat caaattaata aatttttatat tttatatcat gactttctgt tacatttatt    1140
gtgttttcaa gtacatcata caatacatga tcaactgctc tgattacatt gttaatggaa    1200
attacaccaa gactatctaa atacttaaga acttgatatc taaatactct taagaaacga    1260
ccagtctgag gccgtaaggt cgtccagatt tggaagttga gataacattt gtgaatcccc    1320
agtaccttcc tgatattgtg attgaatctt atctgtattg aaatgatgtc gtggctcatt    1380
agaaatggcc tctcgtcgtg gttggtgatc ttgaaatata ggggattttc tatctcccat    1440
ataaaaacgc cattctgggc ttgatgagca gtgatgagtt ccccggtgcg tgaatccatg    1500
attgatgcag ttgatgtgga ggtaatatga gcatccgcag tcgaggtcta tgcgcttacg    1560
tctgactggc ttagtcttcg ctatgcggtg ttggattttg attggcactt gagaacagtg    1620
gctcgtagag ggtgacgaag gttgcattct tgagagccca atttttcaag gatatgtttt    1680
tttcttcgtc tagatattcc ctatatgatg aggtaggtcc tggattgcag aggaagatag    1740
tgggaattcc ccctttaatt tgaatcggct tcccgtactt tgtgttgctt tgccagtccc    1800
tctgggcccc catgaattcc ttgaagtgct ttaaataatg cgggtctacg tcatcgatga    1860
cgttgtacca cgcatcatta ctgtacacct ttggacttag gtctagatgt ccacataaat    1920
aattatgtgg gcctagagac ctggcccaca ttgtcttccc cgttctgcta tcaccctcga    1980
tgacaatact attaggtctc catggccgcg cagcggaaga catgacgttc tcggacaccc    2040
atacttcaag ttcatctgga acttgattaa aagatgaaga taaaaaggga gaaatataag    2100
```

```
gagccggagg ctcctgaaaa attctatcta aatttgaatt taaattatga aattgaagta    2160
taaagtctct aggagctttc tccttcagta tattgagggc ctgagctttg gaccctgaat    2220
tgattgcctc ggcatatgcg tcgttggcag attggcaacc tcctctagct gatcgtccat    2280
cgacttggaa aactccatga tcaatgacgt ctccgtcttt ttccatatag gatttgacat    2340
cgcttgaact cttagctccc tgaatgttcg gatggaaatg tgctgacctg gttggggatg    2400
tgaggtcgaa gaatctgttg tttttgcact ggaactttcc ttcgaactgg atgagcacat    2460
gcaagtgagg agtcccatct tcatgaagct ctctgcagat tctaatgaat tttttggaag    2520
tgggtgtttg tatatttaat aattgggaaa gtgcttcctc tttagttaga gagcatttgg    2580
gataagtgag aaaataattt ttggcattta ttttaaaccg attgggggct gccatattga    2640
cttggtcaat cggagtctct caactctttc tatgtattgg tgtattggag tcctatatat    2700
atggagactc caatggcata tatgtaaata ttgtacttta attcaaaatc atcacgctcc    2760
aaaaagc                                                             2767

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer Cas9-gw-Fw

<400> SEQUENCE: 102
caccatggac tataaggacc acg                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer Cas9-Rev-Stop

<400> SEQUENCE: 103
ttactttttc ttttttgcct ggc                                              23

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer Cas9-Rev-No-Stop

<400> SEQUENCE: 104
cttttctttt tttgcctggc                                                  20

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-ACTIN1-RT-F
```

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-ACTIN1QRT-LIU-R

<400> SEQUENCE: 106
ttgtatgtgg tctcgtggat tc                                             22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer CAS9-SEQ-F6

<400> SEQUENCE: 107
gccctccaaa tatgtgactt cc                                             22

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer CAS9-REV-STOP

<400> SEQUENCE: 108
ttactttttc tttttgcct ggc                                             23

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV1-RELICASE-RT-F

<400> SEQUENCE: 109
ctactgggag agcagcaacc                                                20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer TRV1-REPLICASE-RT-R

<400> SEQUENCE: 110
ctgagcgcaa aagtacacca                                                20

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer SPDK-PEBVS/SEQF

<400> SEQUENCE: 111
cgaattcgag catcttgttc tggggtttca                                      30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer SPDK-SEQ-R

<400> SEQUENCE: 112
ctatggtaag acaatgagtc ggccaaacgc                                      30

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-PDS3-TR1,2-GDNA-F2

<400> SEQUENCE: 113
gaaacacatc acctaggcgg                                                 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB-PDS3-TR1,2-GDNA-R

<400> SEQUENCE: 114
gggcgtgagg aagtacgaaa                                                 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB.PCNA gDNA F1

<400> SEQUENCE: 115 cctaaccta atttccccag                                                  20

<210> SEQ ID NO 116
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer NB.PCNA gDNA R1

<400> SEQUENCE: 116
tcactgtcaa tgtccatcag                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: IR-gRNA

<400> SEQUENCE: 117
ggccatccgt ataatattac                                               20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CP-gRNA

<400> SEQUENCE: 118
cttcggcgaa ccttcgagac                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RCRII-gRNA

<400> SEQUENCE: 119
tggatgagca catgcaagtg                                               20
```

METHOD OF INHIBITING PLANT VIRUS PATHOGEN INFECTIONS BY CRISPR/CAS9-MEDIATED INTERFERENCE

CROSS-REFERENCE TO RELATED APPLICATIONS

This application is a National Stage Application of PCT/IB2016/052918, filed on May 18, 2016, which claims benefit of Application No. 62/162,856, filed on May 18, 2015 in the United States and which applications are incorporated herein by reference. A claim of priority to all, to the extent appropriate, is made.

FIELD OF THE DISCLOSURE

The present disclosure relates to methods of inhibiting viral infections of a plant by delivering a viral-specific sgRNA to a plant cell expressing Cas9 endonuclease.

SEQUENCE LISTING

The present disclosure includes a sequence listing filed in electronic form as an ASCII.txt file entitled 4053_146USWO_SL.txt, the content of which is incorporated herein by reference in its entirety. Said ASCII copy, created on Dec. 5, 2017, is 36,137 bytes in size.

BACKGROUND

Geminiviruses threaten food security and agriculture, infecting key crop species, especially in tropical and subtropical regions (Gilbertson et al., Ann. Rev. Virol 0.2, 67-93 (2015)). Geminiviruses are characterized by their twin icosahedral capsids and small, single-stranded DNA (ssDNA) genome (approximately 2.7 kb) (Hanley-Bowdoin et al., Nat. Revs. Microbiol. 11, 777-788 (2013)). A study examining genome-wide pairwise sequence identity, genome organization, host range, and insect transmission vector recently classified the family Geminiviridae into seven genera: *Begomovirus, Curtovirus, Topocuvirus, Mastrevirus, Becurtovirus, Turncurtovirus*, and Eragroviru (Varsani et al., Arch. Virol. 1-11 (2014)). Begomoviruses infect dicotyledonous plants via the silverleaf whitefly (*Bemisia tabaci*) vector. The genomes of Begomoviruses are composed of one (A, monopartite) or two (A and B, bipartite) components. The A and B components of the virus share a common region with nearly identical nucleotide sequences (Fondong, V. N. Mol. Plant Pathol. 14, 635-649 (2013)).

Effective strategies for controlling geminiviruses remain expensive and inefficient due to mixed virus infections and the patho-interaction of vectors, viruses, and host plants (Gilbertson et al., Development of Integrated Pest Management (IPM) Strategies for Whitefly (*Bemisia tabaci*)-Transmissible Geminiviruses. 323-356 (2011)). However, recent work showed that site-specific nucleases can directly target and cleave the viral genome. This cleavage of the viral genome leads to the generation of double strand breaks (DSBs), which are either repaired by the imprecise non-homologous end-joining repair (NHEJ) machinery or by precise homology-directed repair (HDR) (Ebina et al., *Sci. Rep.* 3, 2510 (2013); Ali et al., *Genome Biol.* 16, 1-11 (2015); Aouida et al., *Curr. Genet.* 60, 61-74 (2014)). The presence of unrepaired DSBs ultimately leads to degradation of the virus molecules (Zaidi et al., *Trends Plant Sci.* 21, 279-281 (2016)). Virus variants generated by NHEJ can replicate and move systemically only if NHEJ maintains the proper "frame" for translation and does not compromise protein function. Several site-specific nuclease platforms have been developed with potential applications for targeted interference against viral genomes.

Clustered regularly interspaced palindromic repeats (CRISPR)/CRISPR-associated 9 (Cas9) is an adaptive molecular immunity system used by bacteria and Archaea to fend off invading phages and conjugative plasmids (Wright et al., Cell 164, 29-44 (2016); Hsu et al., Cell 157, 1262-1278 (2014); Barrangou et al., Science 315, 1709-1712 (2007)). The CRISPR/Cas9 system has been harnessed for targeted mutagenesis and genome editing of eukaryotic genomes, including plants (Liu et al., Curr. Opinion Plant Biol. 30, 70-77 (2016); Nekrasov et al., Nat. Biotech. 31, 691-693 (2013); Cong et al., Science 339, 819-823 (2013); Mali et al., Science 339, 823-826 (2013); Ali et al., Mol. Plant 8, 1288-1291 (2015)).

The CRISPR/Cas9 machinery is composed of Cas9 (a site-specific DNA endonuclease) and a synthetic single guide RNA (sgRNA, alternatively designated gRNA). The sgRNA, which carries 20-nucleotides of target sequence information, is used to direct the Cas9 endonuclease to its genomic target sequence, which must precede a tri-nucleotide sequence known as the protospacer-associated motif (PAM). *Streptomyces pyogenes* Cas9 recognizes the PAM sequence NGG and cleaves three nucleotides preceding this PAM sequence on complementary and non-complementary strands (Wright et al., Cell 164, 29-44 (2016); Hsu et al., Cell 157, 1262-1278 (2014); Barrangou et al., Science 315, 1709-1712 (2007); Cong et al., Science 339, 819-823 (2013); Mali et al., Science 339, 823-826 (2013)). Cas9 variants with improved specificity have recently been characterized (Zetsche et al., Cell 163, 759-771 (2015); Slaymaker et al., Science 351, 84-88 (2016); Davis et al., Nat. Chem. Biol. 11, 316-318 (2015); Kleinstiver et al., Nature 523, 481-485 (2015)).

It the portability of the CRISPR/Cas9 machinery to confer molecular immunity against eukaryotic viruses, including plant DNA viruses (Karimova et al., Sci. Rep. 5, 13734 (2015); Lin et al., Mol. Ther. Nucl. Acids (2014); Ramanan et al., Sci. Reports 5, 10833 (2015); Hu et al., Proc. Natl. Acad. Sci. U.S.A. 111, 11461-11466 (2014); Chaparro-Garcia et al., Genome Biol 16, 254 (2015)). CRISPR/Cas9 machinery can target coding and non-coding sequences of different geminiviruses (Baltes et al., Nat. Plants 1, 15145 (2015); Ji et al., Nat. Plants 1, 15144 (2015)). This targeting results in reduced viral accumulation and delayed or abolished symptoms. However, different sgRNAs have different targeting efficiencies for coding or noncoding sequences. Numerous reports describe the emergence of geminiviruses with altered pathogenicity and subsequent changes in the severity of disease symptoms in infected plants, resulting from recombination-mediated genetic changes or reassortment among different viral genomes. Targeting the viral genome opens up various possibilities, including degradation and/or repair of these genomes. Under natural field conditions, where mixed viral infections exist, targeting a single virus, generating DSBs, and initiating cellular repair could induce recombination or generation of viral variants capable of replication and survival. Since the nature of the target viruses largely determines the efficiency of interference by the CRISPR/Cas9 system, production of durable resistance requires the establishment of criteria for selecting which virus sequences to target.

It has proven difficult and expensive to control or manage the disease caused by the Tomato Yellow Leaf Curl Virus (TYLCV). Several approaches for disease resistance focus on insecticide treatments of the viral transmission vector whitefly (*Bemicia tabaci*) (Lapidot et al., (2014) Advances Virus Res. 90: 147-206). Breeding for resistance is challenging due to the linkage of genes of poor fruit quality to the resistance locus. Several attempts have been made to engineer tomato for resistance to TYLCV including the over-expression of the viral proteins CP, C4, or the IR noncoding sequences (Yang et al., (2004) Phytopathol. 94: 490-496). It has been shown that binding to the origin of replication by the replication protein (Rep) interferes with the viral replication and lead to viral resistance. Synthetic zinc finger protein has been used to block the Rep protein of the beet severe curly top virus (BSCTV) from binding to the origin of replication resulting in virus resistance (Sera T. (2005) J. Virol. 79: 2614-2619). Moreover, such technology was applied to TYLCV through the interference with the Rep protein binding to the origin of replication (Koshino-Kimura et al., (2009) Nucleic Acids Symp. Series 53: 281-282; Mori et al., (2013) Mol. Biotech. 54: 198-203). Nevertheless, effective means to control or manage the TYLCV disease has proven challenging. Therefore, developing effective technologies for viral resistance is needed to increase the yield of crop species (Galvez et al., (2014) Plant Sci. 228: 11-25)).

SUMMARY

The CRISPR/Cas9 system can be used for targeted genome modification and regulation across diverse eukaryotic species. The present disclosure demonstrates the use of imparting this system for in planta viral interference. The data show that a CRISPR/Cas9 system can be used for targeted interference and cleavage of geminivirus genomes including, but not limited to, the TYLCV genome. Targeting the TYLCV IR region showed significant reduction of TYLCV accumulation and symptoms. The CRISPR/Cas9-mediated interference is virus strain-specific and can be used to target multiple viruses. The data reveal that it possible to use the CRISPR/Cas9 system to engineer plants for resistance against DNA viruses.

One aspect of the disclosure encompasses embodiments of a genetically modified plant resistant to at least one pathogenic virus species, said plant comprising a heterologous CRISPR/Cas9 system and at least one heterologous nucleotide sequence that is capable of hybridizing to a nucleotide sequence of the pathogenic virus under stringent conditions, or to a complement thereof, and that directs inactivation of the pathogenic virus species or plurality of viral species by the CRISPR/Cas9 system.

In some embodiments of this aspect of the disclosure, the pathogenic virus is of the geminiviridae. In some embodiments of this aspect of the disclosure, the pathogenic virus can be of the geminiviridae genus *Becurtovirus, Begomovirus, Curtovirus, Eragrovirus, Mastrevirus, Topocuvirus* or *Turncurtovirus*.

In some embodiments of this aspect of the disclosure, the pathogenic virus can be selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV).

In some embodiments of this aspect of the disclosure, the plant is a tobacco plant or a tomato plant.

In some embodiments of this aspect of the disclosure, the at least one heterologous nucleotide sequence is capable of hybridizing under stringent conditions to a nucleotide sequence of the pathogenic virus, or to a complement thereof, and wherein the nucleotide sequence of the pathogenic virus is an Intergenic Region (IR) or an Open Reading Frame (ORF).

In some embodiments of this aspect of the disclosure, the at least one heterologous nucleotide sequence is capable of hybridizing under stringent conditions to a nucleotide sequence of an Intergenic Region (IR) of the pathogenic virus, or to a complement thereof.

In some embodiments of this aspect of the disclosure, the at least one heterologous nucleotide sequence is capable of hybridizing under stringent conditions to a nucleotide sequence of an Intergenic Region (IR) of the Tomato Yellow Leaf Curl Virus (TYLCV), or to a complement thereof.

In some embodiments of this aspect of the disclosure, the at least one second heterologous nucleotide sequence has the nucleic acid sequence 5'-GGCCATCCGTATAATATTAC-3' (SEQ ID NO: 75).

In some embodiments, a genetically modified plant is provided according to any one or more of the foregoing embodiments.

Another aspect of the disclosure encompasses embodiments of a method of generating a genetically modified plant resistant to a virus pathogen, the method comprising the steps of: (a) obtaining a plant susceptible to a pathogenic virus, wherein said plant is genetically modified to express a heterologous CRISPR/Cas9 system; and (b) genetically modifying said plant to include at least one heterologous nucleotide sequence capable of hybridizing under stringent conditions to a nucleotide sequence of the pathogenic virus, or to a complement thereof, and wherein the at least one heterologous nucleotide sequence can direct inactivation of the virus pathogen by the CRISPR/Cas9 system.

BRIEF DESCRIPTION OF THE DRAWINGS

Many aspects of the disclosure can be better understood with reference to the following drawings.

FIG. 1B schematically illustrates the experimental protocol for demonstrating the use of CRISPR/Cas9 system to reduce viral infections in a plant.

FIG. 2C illustrates an alignment of Sanger sequencing reads (SEQ ID NOs: 69-74) indicating that 28% of the clones carry targeted modifications within the IR sequence.

FIG. 2D illustrates an alignment of Sanger sequencing reads (SEQ ID NOs: 62-68) indicating that different ORFs can be targeted for modification and used to interfere with TYLCV accumulation.

FIG. 3A illustrates the sequences of TYLCV (SEQ ID NO: 75) and Beet Curly Top Virus (BCTV) strain Worland-specific (SEQ ID NO: 76) IR-sgRNAs.

FIG. 3B illustrates the results of a restriction site loss assay confirming that a TYLCV-specific IR-sgRNA and not Beet Curly Top Virus (BCTV) strain Worland-specific IR-sgRNA can target any sequence similar to TYLCV IR region and thereby interfere with genome replication.

FIG. 3C illustrates alignments of Sanger sequencing reads (SEQ ID NOs: 77-88) indicating that different ORFs can be targeted for modification and used to interfere with TYLCV-specific accumulation.

FIG. 4A illustrates that WOR-RCRII-sgRNA targeted the Worland genome but not TYLCV genome.

FIG. 4B illustrates sequences SEQ ID NOs: 89-94.

FIG. 4C illustrates sequences SEQ ID NOs: 95-100.

FIG. 6 illustrates the TYLCV 2.3 genome sequence SEQ ID NO: 101. The IR, CP and RCR-II target sequences are shown in bold underlined.

FIGS. 7A-7F illustrate CRISPR/Cas9-mediated targeting of coding and non-coding sequences of the CLCuKov genome.

FIG. 7A illustrates the genome organization of Cotton Leaf Curl Kokhran Virus (CLCuKov) and Cotton Leaf Curl Multan Betasatellite (CLCuMβ). Bidirectional and overlapping ORFs (CP, Rep, Ren, TrAP, V2, and C4) are represented by arrows, the IR is represented by a box, stem loop with nonanucleotide is represented by a small circle in the IR and SCR, and targets are represented by arrowheads and individual sequences. The selected targets, one in non-coding IR, one each in coding CP or in the Rep RCRII domain, were analyzed for CRISPR/Cas9-mediated targeting followed by NHEJ repair.

FIG. 7B illustrates NHEJ repair (indel) analysis via the T7EI assay. Arrow indicates the presence of 255 bp and 191 bp regions only in samples expressing CP-sgRNA, but not in samples with TRV empty vector or virus alone.

FIG. 7C illustrates alignment of reads of PCR amplicons (SEQ ID NOs: 1-6) encompassing the CP region and subjected to Sanger sequencing for indel (NHEJ repair) confirmation.

FIG. 7D illustrates T7EI assay for detecting indels in the RCRII domain of the CLCuKov genome. The T7EI assay detected mutations only in RCRII PCR amplicons from plants infiltrated with TRV containing RCRII-sgRNA, but not in plants infiltrated with TRV empty vector or virus alone.

FIG. 7E illustrates alignment of reads of the PCR amplicons (SEQ ID NOs: 7-11) encompassing the RCRII motif and subjected to Sanger sequencing for NHEJ repair confirmation.

FIG. 7F illustrates NHEJ repair analysis at the IR sequence by restriction site loss assay. The CLCuKov IR (446 bp) was analyzed for the loss of the SspI recognition site through NHEJ (indels). The arrow indicates the expected SspI-resistant 446 bp DNA fragment; none of the samples produced the SspI-resistant DNA fragment, which is similar to TRV empty vector or virus alone.

All DNA fragments from FIGS. 7B, 7D, and 7F were resolved on a 2% agarose gel premixed with ethidium bromide stain. Arrows in FIGS. 7B, 7D, and 7F represent the expected DNA fragments. The indel percentage shown below each gel was calculated based on the Sanger sequence reads. In FIG. 7C (reverse strand sequence) and FIG. 7F, the wild-type (WT) sequences, shown at the top lines thereof, the target sequence is boxed; the protospacer-associated motif [PAM] is underlined, followed by the various indels formed, as indicated by numbers to the right of the sequence (−, deletion of x nucleotides; +, insertion of x nucleotides; and >, change of x nucleotides to y nucleotides).

FIGS. 8A-8F illustrate NHEJ repair of coding and non-coding sequences of the MeMV genome. Non-coding IR, coding CP, and the Rep RCRII domain of MeMV were analyzed for NHEJ repair.

FIG. 8A illustrates NHEJ repair (indel) analysis via an SspI recognition site loss assay. The MeMV IR (453 bp) was analyzed for the loss of the SspI recognition site at the CRISPR/Cas9 target locus. Unlike CLCuKov, NHEJ-repaired indels are indicated by arrows pointing to the 453-bp SspI-resistant DNA fragments.

FIG. 8B illustrates alignment of reads of PCR amplicons (SEQ ID NOs: 12-16) encompassing the IR of MeMV subjected to Sanger sequencing for NHEJ repair confirmation.

FIG. 8C illustrates T7EI assay to detect indels in the CP of the MeMV genome. The T7EI assay detected indels only in CP PCR amplicons from plants infiltrated with TRV containing the CP-sgRNA, but not in plants infiltrated with TRV empty vector or virus alone.

FIG. 8D illustrates alignment of reads of the PCR amplicons (SEQ ID NOs: 17-21) encompassing the target site and subjected to Sanger sequencing for NHEJ repair confirmation.

FIG. 8E illustrates NHEJ repair analysis at the RCRII motif of MeMV by T7EI assay. Arrow indicates the expected DNA fragments; TRV empty vector or virus alone did not show similar fragments.

FIG. 8F illustrates alignment of reads of the PCR amplicons (SEQ ID NOs: 22-26) encompassing the target site and subjected to Sanger sequencing for NHEJ repair confirmation.

All DNA fragments in FIGS. 8A, 8C, and 8E were resolved on a 2% agarose gel premixed with ethidium bromide stain. Arrows in FIGS. 8A, 8C, and 8E indicate the expected DNA fragments. The indel percentage shown below each gel was calculated based on the Sanger sequence reads. In FIGS. 8B, 8D, and 8F, the wild-type (WT) sequences, shown at the top lines thereof, the target sequence is boxed; the protospacer-associated motif [PAM] is underlined, followed by the various indels formed, as indicated by numbers to the right of the sequence (−, deletion of x nucleotides; +, insertion of x nucleotides; and >, change of x nucleotides to y nucleotides).

FIG. 9A illustrates the stem-loop structures (SEQ ID NOs: 27-32) of the different geminiviruses used in this study. The conserved nonanucleotide motif is flanked on each side by a short stretch of complementary sequences.

FIG. 9B illustrates restriction site loss assay for detecting NHEJ-based indels at the IR of TYLCSV. The TYLCSV IR (562 bp) was analyzed for the loss of the SspI recognition site at the targeting locus. The arrow indicates the location of the expected 562-bp SspI-resistant DNA fragment in samples with IR-sgRNA, but like TRV empty vector and virus alone, no SspI-resistant fragment was observed.

FIG. 9C illustrates SspI recognition site loss assay for detecting indels at the IR in TYLCV2.3. The variant TYLCSV-IRsgRNA (two lanes after marker) and authentic TYLCV2.3-IRsgRNA (last three lanes) were used to target the IR of TYLCV2.3. Arrows indicate the presence of the expected 269 bp SspI-resistant DNA fragments in samples with TYLCV2.3-IR-sgRNA or TYLCSV-IRsgRNA, but no SspI-resistant fragment was observed in TRV empty vector.

FIG. 9D illustrates a T7EI assay for detecting NHEJ-based indels in the CP and RCRII domain of the TYLCSV genome. T7EI assay detected high rates of indel formation both in CP and RCRII PCR amplicons from plants infiltrated with TRV containing CP or RCRII-sgRNA compared with TRV empty vector.

Figure 9A:
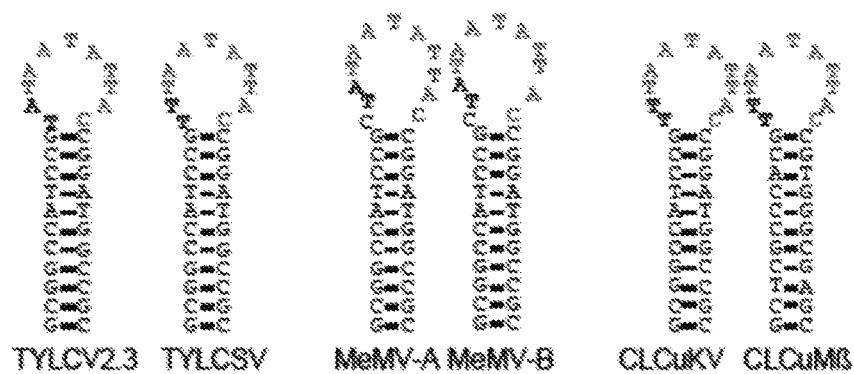
FIGS. 9A-9D illustrate variable efficiencies of indel formation at the IR sequences of different strains of TYLCV.
Figure 9B:
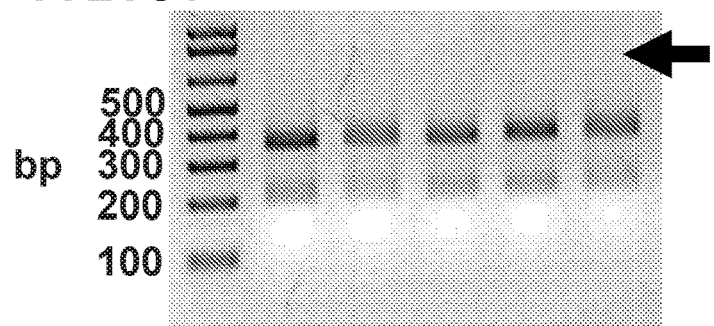
Figure 9C:
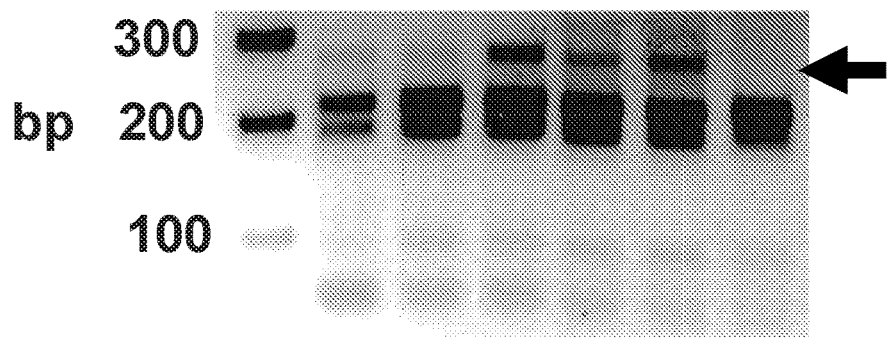
Figure 9D:
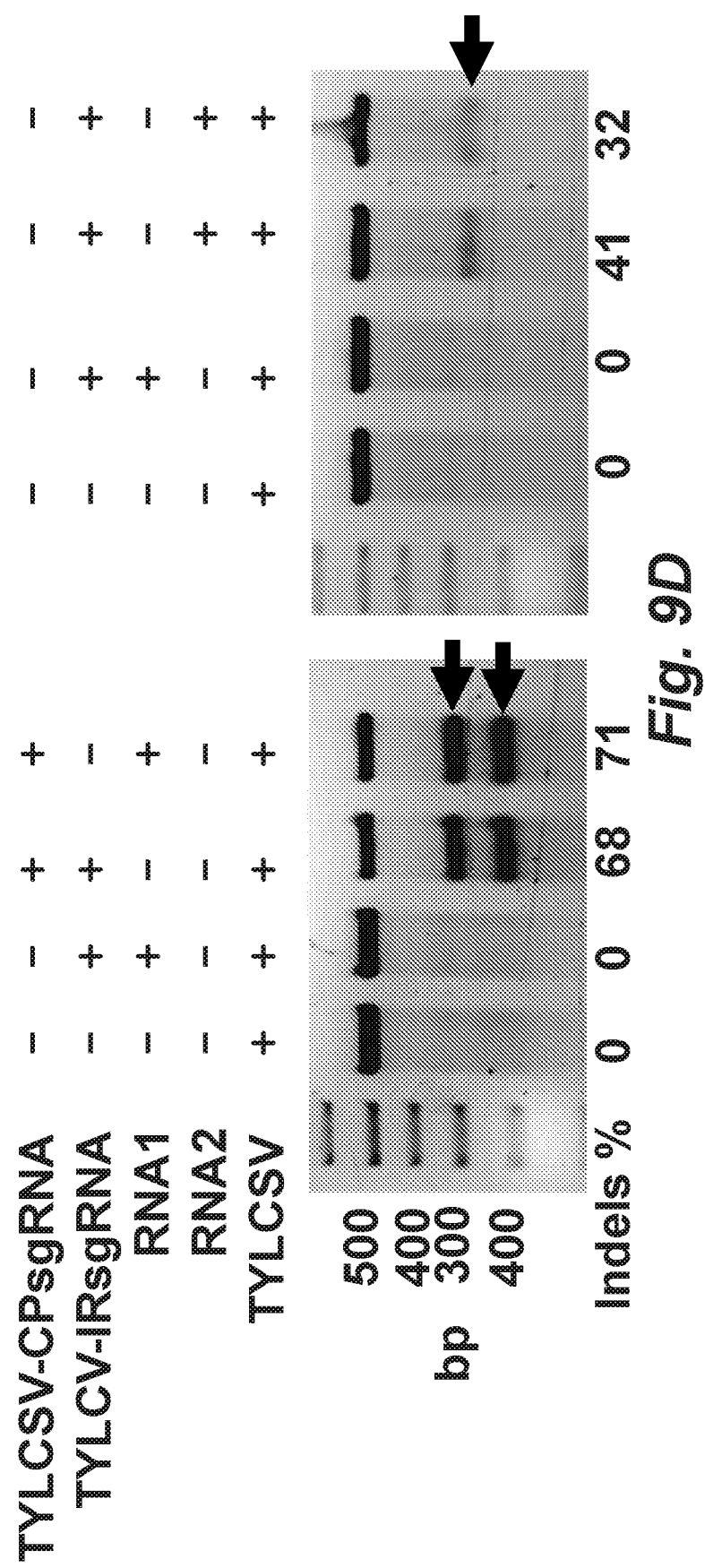

DNA fragments of FIGS. 9B, 9C, and 9D were resolved on a 2% agarose gel stained with ethidium bromide. Arrows represent the expected DNA fragment in T7EI-digested DNA. The indel percentage shown below each gel was calculated based on the Sanger sequence reads.

FIGS. 10A-10C illustrate IR targeting by CRISPR/Cas9 interferes with genome accumulation of both CLCuKov and TYLCSV.

DNA blot analysis assaying CLCuKov (FIG. 10A) and TYLCSV (FIG. 10B) genomic DNA accumulation in Cas9OE plants expressing CLCuKov-IRsgRNA and TYLCSV-IRsgRNA, respectively. CLCuKov and TYLCSV genomic DNA was detected with DIG-labeled probe produced against the respective IRs of CLCuKov and TYLCSV. All individual plants with IR-sgRNA that were infiltrated with CLCuKov and TYLCSV exhibited reduced accumulation of the genomes relative to plants inoculated with TRV empty vector and virus only. Arrowheads in FIGS. 10A and 10B indicate detection of the expected size of the TYLCV genome.

FIG. 10C illustrates an alignment of cloned Sanger-sequenced PCR amplicons (SEQ ID NOs: 33-36) encompassing the IR of CLCuKov. Alignment of sequence reads encompassing the IR shows only long deletions. The wild-type (WT) CLCuKov sequence is shown at the top; the various indels formed are indicated by numbers in the middle of the sequence reads.

FIGS. 11A-11E illustrate NHEJ-repaired CP sequence evades CRISPR/Cas9.

Figure 11A:
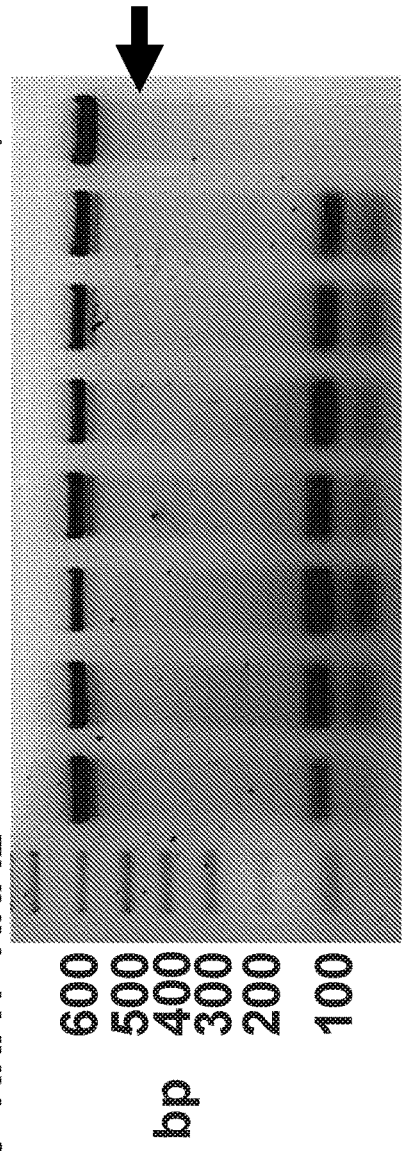

FIG. 11A illustrates evasion of repaired CP sequence of TYLCV genomes, as revealed by the T7EI assay. Sap from TYLCV-infected plants with an established CRISPR/Cas9 system against the CP region was applied to WT N. benthamiana plants. Total genomic DNA was isolated from top (young) leaves of sap-inoculated WT plants at 15 DAI. CP targets flanking PCR amplicons were subjected to T7EI. Arrows indicate the presence of the expected digested DNA fragment from samples of CP-targeted sap-infected plants compared to TRV empty vector with TYLCV.

Figure 11B:
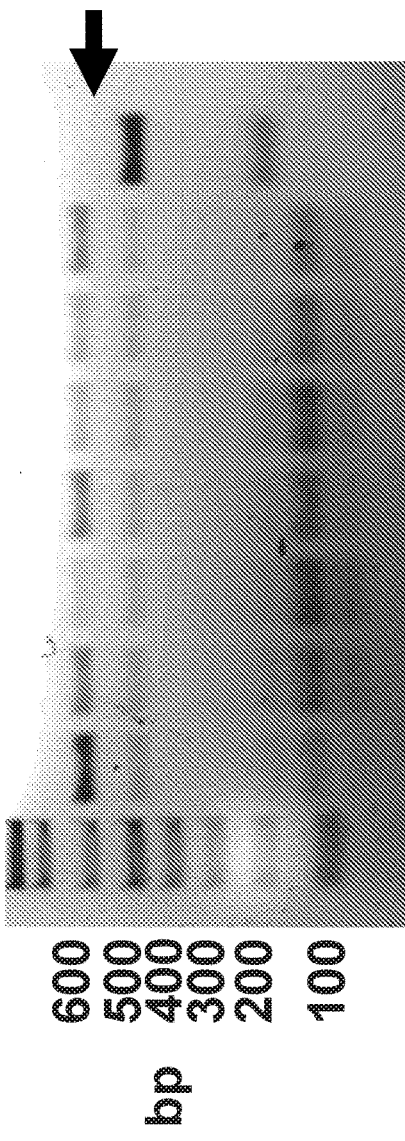

FIG. 11B illustrates BsmBI-recognition site loss assay for detecting escapees. Initially, PCR amplicons were treated with BsmBI to enrich the CRISPR/Cas9 escapees. BsmBI-treated PCR fragments were used as template in another round of PCR with the same primers. Purified DNA from this PCR was again subjected to BsmBI digestion. Arrowheads indicate the expected BsmBI-resistant DNA fragments compared to WT PCR amplicons from TRV empty vector. DNA fragments of A and B were resolved on a 2% agarose gel stained with ethidium bromide.

FIG. 11C illustrates alignment of Sanger-sequencing reads of PCR amplicons (SEQ ID NOs: 37-42) encompassing the CP region of TYLCV for mutation at the CRISPR/Cas9 targeting site. The wild-type (WT) TYLCV sequence is shown at the top, the target sequence is boxed, the BsmBI site is indicated by a line, and the protospacer-associated motif [PAM] is indicated; the various mutations are shown in enlarged, bold at their respective sites.

FIG. 11D illustrates evasion analysis of TYLCSV genomes with repaired CP sequences via the T7EI assay. TYLCSV samples were prepared as in FIG. 11A. CP targets flanking the PCR amplicons were subjected to T7EI. Arrows indicate the presence of the expected digested DNA fragments from samples of CP-targeted sap-infected plants compared to TRV empty vector with TYLCSV.

FIG. 11E illustrates evasion analysis of genomes of CLCuKov genomes with repaired CP sequences via the T7EI assay. Wild-type scions were grafted to the stocks of CLCuKov-infected plants with an established CRISPR/Cas9 system against the CP region. Total genomic DNA was isolated from top (young) leaves of WT scions at 21 DAI. CP-target-flanking PCR amplicons were subjected to T7EI. Arrows indicate the presence of the expected digested DNA fragment from samples of CP-targeted CLCuKov compared to TRV empty vector with CLCuKov.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "CRISPR" and "CRISPR Genome Engineering" as used herein refers to the Clustered Regularly Interspaced Short Palindromic Repeats (CRISPR) Type II system which is the most commonly used RNA-Guided Endonuclease technology for genome engineering. There are two components to this system: (1) a guide RNA and (2) an endonuclease, in this case the CRISPR associated (Cas) nuclease, Cas9.

Guide RNA is a combination of the targeting specificity of endogenous bacterial crRNA and the scaffolding properties of tracrRNA into a single chimeric guide RNA (sgRNA) transcript. When the sgRNA and the Cas9 are expressed in a cell, the genomic target sequence can be modified or permanently disrupted.

The sgRNA/Cas9 complex is recruited to a target sequence by the base-pairing between the sgRNA sequence and the complement to the target sequence in the genomic DNA. For successful activity of Cas9, the genomic target sequence must also contain the correct Protospacer Adjacent Motif (PAM) sequence immediately following the target sequence. The binding of the sgRNA/Cas9 complex localizes the Cas9 to the genomic target sequence so that the wild-type Cas9 can cut both strands of the DNA causing a Double Strand Break (DSB).

A DSB can be repaired through one of two repair pathways: (1) the Non-Homologous End Joining (NHEJ) DNA repair pathway or (2) the Homology Directed Repair (HDR) pathway. The NHEJ repair pathway typically results in inserts/deletions (InDels) at the DSB site that can lead to frameshifts and/or premature stop codons, effectively disrupting the open reading frame (ORF) of the targeted gene. The HDR pathway requires the presence of a repair nucleic acid template, which is used to fix the DSB. HDR faithfully copies the sequence of the repair template to the cut target sequence. Specific nucleotide changes can be introduced into a targeted gene by the use of HDR with a repair template carrying the desired change.

The term "Cas9 nuclease" as used herein refers to an endonuclease having two functional domains: RuvC and HNH, each cutting a different DNA strand. When both of these domains are active as in wild-type Cas9, the Cas9 causes double strand breaks (DSBs) in the genomic DNA. In the absence of a suitable repair template, the DSB is then repaired by the Non-Homologous End Joining (NHEJ) DNA repair pathway. During NHEJ repair, InDels (insertions/deletions) can occur as a small number of nucleotides are either inserted or deleted at random at the DSB site, thereby altering the Open Reading Frame (ORF) of the target gene, which may significantly change the amino acid sequence downstream of the DSB. Additionally, InDels can also introduce a premature stop codon either by creating one at the DSB or by shifting the reading frame to create one downstream of the DSB. However, InDels induced by NHEJ are random, so the type and extent of gene disruption will need to be determined experimentally. To maximize the effect of gene disruption, target sequences preferably are chosen near the N-terminus of the coding region of the gene of interest, typically to introduce a DSB within the first or second exon of the gene.

The CRISPR system can also be used to introduce specific nucleotide modifications of the target sequence. Thus, cells can utilize a less error-prone DNA repair mechanism termed "Homology Directed Repair (HDR)."

To introduce nucleotide modifications to genomic DNA, a DNA repair template containing the desired sequence must be provided during HDR. The DNA template is typically transfected into a cell together with the sgRNA/Cas9 and must have a high degree of complementarity to the nucleotide sequences immediately upstream and downstream of the DSB. The length and binding position of each "homology arm" is dependent on the size of the change being introduced. When designing a repair template for genome editing by HDR, the repair template must not contain the target sequence followed by the PAM sequence or the template itself will also be cut by the Cas9. Changing the sequence of the PAM in the repair template likely will prove sufficient to ensure it is not cut by Cas9. Again, the desired modification in the genomic DNA must be confirmed experimentally.

The term "Off-Target Effects" as used herein refer to when flexibility in the base-pairing interactions between the sgRNA sequence and the genomic DNA target sequence allows imperfect matches to the target sequence to be cut by Cas9. Single mismatches at the 5' end of the sgRNA (furthest from the PAM site) can be permissive for off-target cleavage by Cas9.

The term "nickase" as used herein refers to modified versions of the Cas9 enzyme containing a single inactive catalytic domain, either RuvC- or HNH-. With only one active nuclease domain, the Cas9 "nickase" will cut only one strand of the target DNA, thereby generating a single-strand break or 'nick'. A Cas9 nickase is still able to bind DNA based on sgRNA specificity, though nickases will only cut one of the DNA strands. The majority of CRISPR plasmids are derived from *S. pyogenes* and the RuvC domain inactivated, for example, by a D10A mutation.

A single-strand break, or nick, is normally repaired through the HDR pathway, using the intact complementary DNA strand as the template. However, two proximal, opposite strand nicks introduced by a Cas9 nickase are treated as a Double Strand Break (DSB), in what is often referred to as a 'double nick' or 'dual nickase' CRISPR system. A double-nick induced DSB can be repaired by either NHEJ or HDR depending on the desired effect on the gene target. For example, two different sgRNAs can bind in a particular genomic region. When the sgRNAs are co-expressed with a Cas9 nickase, single-strand nicks created in the DNA are quickly repaired by HDR using the intact compliment strand as a template and no change occurs. Nicks in close proximity (and on opposite strands) behave as a DSB. However, by situating two sgRNAs with target sequences in close proximity and on opposite strands of the genomic DNA, off-target effects of either sgRNA alone will result in nicks that will not change the genomic DNA. Only at the target location where both nicks are proximal, will the double nicked sequence be considered a DSB. The double-nickase technique is described in, for example, Ran et al., (2013) Cell 154: 1380-1389.

The Cas9 protein requires the targeting specificity of an sgRNA. Choosing an appropriate target sequence in the genomic DNA is a crucial step in designing an experiment. The target sequence is 20 nucleotides followed by the appropriate Protospacer Adjacent Motif (PAM) sequence in the genomic DNA. Target sequences (20 nucleotides+PAM) can be on either strand of the genomic DNA and can appear in multiple places in the genome. Accordingly a bioinformatic program is helpful to select target sequences and minimize off-target effects. There are a number of tools available to help choose/design target sequences as well as lists of bioinformatically determined (but not experimentally validated) unique sgRNAs for different genes in different species.

The term "Protospacer Adjacent Motif (PAM) Sequence" as used herein refers to a nucleic acid sequence present in the DNA target sequence but not in the sgRNA sequence itself. For Cas9 to successfully bind to DNA, the target sequence in the genomic DNA must be complementary to the sgRNA sequence and must be immediately followed by the correct protospacer adjacent motif or PAM sequence. Any DNA sequence with the correct target sequence followed by the PAM sequence will be bound by Cas9. A target sequence without the PAM following it is not sufficient for Cas9 to cut. Furthermore, the PAM sequence varies by the species of the bacteria from which the Cas9 was derived. The Type II CRISPR system derived from *S. pyogenes*, for example, has the PAM sequence NGG located on the immediate 3' end of an sgRNA recognition sequence and components (sgRNA, Cas9) derived from different bacteria will not function together. The CRISPR system requires that both the sgRNA and Cas9 are expressed in the target cells, the respective promoters for Cas9 and sgRNA expression determining the species specificity of a particular system.

Whichever sequences and hybridization methods are used, one skilled in the art can readily determine suitable hybridization conditions, such as temperature and chemical conditions. Such hybridization methods are well known in the art. For example, for applications requiring high selectivity, one will typically desire to employ relatively stringent conditions for the hybridization reactions, e.g., one will select relatively low salt and/or high temperature conditions, such as provided by about 0.02M to about 0.10M NaCl at temperatures of about 50° C. to about 70° C. Such high stringency conditions tolerate little, if any, mismatch between the probe and the template or target strand, and are particularly suitable for detecting specific SNPs according to the present invention. It is generally appreciated that conditions can be rendered more stringent by the addition of increasing amounts of formamide. Other variations in hybridization reaction conditions are well known in the art (see for example, Sambrook et al., Molecular Cloning; A Laboratory Manual 2d ed. (1989)).

The term "polymerase chain reaction" or "PCR" as used herein refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

The term "primer" as used herein refers to an oligonucleotide, the sequence of at least a portion of which is complementary to a segment of a template DNA which to be amplified or replicated. Typically primers are used in performing the polymerase chain reaction (PCR). A primer hybridizes with (or "anneals" to) the template DNA and is used by the polymerase enzyme as the starting point for the replication/amplification process. By "complementary" it is meant that the nucleotide sequence of a primer is such that the primer can form a stable hydrogen bond complex with the template; i.e., the primer can hybridize or anneal to the template by virtue of the formation of base-pairs over a length of at least ten consecutive base pairs.

The terms "Geminiviridae" and "Geminivirus" as used herein refer to a family of plant viruses. There are about described 325 species in this family, divided among 7 genera. Diseases associated with this family include: bright yellow mosaic, yellow mosaic, yellow mottle, leaf curling, stunting, streaks, and reduced yields. They have single-stranded circular DNA genomes encoding genes that diverge in both directions from a virion strand origin of replication (i.e. geminivirus genomes are ambisense). According to the Baltimore classification they are considered class II viruses. It is the largest known family of single stranded DNA viruses.

*Mastrevirus* transmission is via various leafhopper species (e.g. maize streak virus and other African streak viruses are transmitted by Cicadulina mbila), curtoviruses and the only known *topocuvirus* species, Tomato pseudo-curly top virus, are transmitted by treehopper species (e.g.Tomato pseudo-curly top virus is transmitted by the treehopper Micrutalis malleifera), and begomoviruses are transmitted by the whitefly species, *Bemisia tabaci*.

The genome can either be a single component between 2500-3100 nucleotides, or, in the case of some begomoviruses, two similar-sized components each between 2600 and 2800 nucleotides. Begomoviruses with two component (i.e. bipartite) genomes have these components separated into two different particles both of which must usually be transmitted together to initiate a new infection within a suitable host cell.

Geminivirus genomes encode only a few proteins; thus, they are dependent on host cell factors for replication: these include factors such as DNA polymerase, and probably repair polymerases, to amplify their genomes, as well as transcription factors. Geminiviruses replicate via a rolling circle mechanism like bacteriophages such as M13, and many plasmids. Replication occurs within the nucleus of an infected plant cell. First the single-stranded circular DNA is converted to a double-stranded circular intermediate. This step involves the use of cellular DNA repair enzymes to produce a complementary negative-sense strand, using the viral genomic or plus-sense DNA strand as a template. The next step is the rolling circle phase, where the viral strand is cleaved at a specific site situated within the origin of replication by the viral Rep protein in order to initiate replication. This process in a eukaryotic nucleus can give rise to concatemeric double-stranded forms of replicative intermediate genomes, although double-stranded unit circles can be isolated from infected plants and cells. New single-stranded DNA forms of the virus genome (plus-sense) are probably formed by interaction of the coat protein with replicating DNA intermediates, as genomes lacking a CP gene do not form ssDNA. The ssDNA is packaged into germinate particles in the nucleus. It is not clear if these particles can then leave the nucleus and be transmitted to surrounding cells as virions, or whether ssDNA associated with coat protein and a movement protein is the form of the genome that gets trafficked from cell to cell via the plasmodesmata.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Abbreviations

CRISPR: Clustered Regularly Interspaced Short Palendromic Repeat (a region in bacterial genomes used in pathogen defense; crRNA: endogenous bacterial RNA that confers target specificity, requires tracrRNA to bind to Cas9; DSB: Double Strand Break; sgRNA (gRNA): guide RNA, a fusion of the crRNA and tracrRNA; sgRNA sequence: 20 nucleotides that precede a PAM sequence in the genomic DNA; HDR: Homology Directed Repair; InDel: Insertion/Deletion; NHEJ: Non-Homologous End-Joining; ORF: Open Reading Frame; PAM: Protospacer Adjacent Motif; IR, non-coding intervening region; CR, coding region; CP, coat protein Description The present disclosure encompasses embodiments of a method for genetically modifying a plant so as to confer to the plant resistance to a viral pathogen or a plurality of viral pathogens. It is contemplated that the plant will have been genetically modified to express the components of the CRISPR/Cas9 system by methods that are known in the art or as described in Example 7 of the present disclosure. The generation of such a plant is not restricted to only a tobacco or tomato plant but may be adapted to any plant species that is desired to modify to have a resistance to a viral pathogen.

The methods of the disclosure further include the step of identifying within the genome of a target virus pathogen a nucleotide sequence that may be isolated and delivered to the CRISPR/Cas9-expressing plant cells for an encounter with the infecting viral particles. Especially advantageously, the methods of the disclosure are useful against infections of plants by species of geminiviridae. It is contemplated that such virus pathogens can be, but are not limited to, member species of the genera *Becurtovirus, Begomovirus*, Curtovirus, Eragrovirus, *Mastrevirus, Topocuvirus* or *Turncurtovirus*, and most advantageously directed against the pathogens Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV). An especially significant pathogenic virus that can be targeted by the methods of the present disclosure is Tomato Yellow Leaf Curl Virus (TYLCV).

It is further contemplated that the nucleotide sequences derived from the targeted virus genome may be used to make transgenic, and thereby stably generate genetically modified plants that are able to counteract an infection by a virus pathogen. By this means, it is possible to provide a population of protected plants such that an agricultural production of the plant is resistant to the invasive virus pathogen. It is within the scope of the present disclosure, therefore, for the method to incorporate delivering the viral nucleotide sequence(s) as sgRNA by such means well-known in the art as a viral vector systemically delivered to a parent plant, by a mechanical means requiring damaging the outer wall of cells of a recipient plant tissue, by in vitro transformation and subsequent growth of the transformed cells to a mature plant, and the like.

The disclosure further provides embodiments of genetically modified plants that are transformed (most advantageously stably transformed) to express a heterologous endonuclease Cas9 and the single strands of nucleic acid that are complementary to a region of the target virus and which enable the endonuclease 9 to cleave the target viral genome, thereby inactivating the virus and reducing the level of the infection in the plant.

The CRISPR/Cas9 system provides molecular immunity to bacteria and archaea against invading phages and conjugative plasmids and has been adapted for targeted genome editing across diverse eukaryotic species. The methods of the present disclosure adapt the CRISPR/Cas9 system to function as molecular immunity machinery directed specifically against DNA viruses. The system according to the disclosure was functionally verified as operable against such as Tomato Yellow Leaf Curly Virus (TYLCV) infections. Thus, while not intending to be limiting as to the geminivirus target, sgRNAs specifically targeted to TYLCV sequences were introduced into a Cas9 overexpressing *Nicotiana benthamiana* plants. Subsequently, the *N. benthamiana* plants were challenged with TYLCV.

The data obtained from using the above system shows that the CRISPR/Cas9 system targeted TYLCV for degradation and/or introduced mutations at the target sequences. Several sgRNAs were tested for activity against TYLCV. A sgRNA targeting the intergenic region (IR) showed advantageous interference levels against TYLCV and exhibited delayed and/or reduced accumulation of viral DNA. The majority of recipient plants were showing either no symptoms or significantly attenuated symptoms. Moreover, it was found that the systems of the disclosure can be highly target-specific. Thus plants challenged with geminiviruses other than TYLCV were not protected. Cumulatively the data of the disclosure establish the efficacy and extend the utility of the CRISPR/Cas9 system to be advantageous for viral interference in plants and provide a mechanism for the generation of genetically modified plants that are resistant to multiple viral infections.

TYLCV is a single-stranded DNA virus (ssDNA), with a genome size of approximately 2.7 kb that replicates in a rolling circle mechanism through a double stranded DNA (dsDNA) intermediate (Moriones & Navas-Castillo (2000) Virus Res. 71: 123-134; Czosnek et al., (1993) Plant Mol. Biol. 22: 995-1005). The genomic structure of TYLCV is composed of 6 partially, bi-directionally organized, overlapping open reading frames (ORF) with intergenic region (IR) containing the origin of replication (Gafni Y. (2003) Mol. Plant Pathol. 4: 9-15). Geminiviruses do not have their own DNA polymerase but reactivate the host cellular S-phase and replication machinery to enable the replication of their own genome. Upon infections of plant cells, the Rep protein binds to the origin of replication and the replication process starts in the plant cell nucleus (Gafni Y. (2003) Mol. Plant Pathol. 4: 9-15). It has been shown that the replication occurs through dsDNA intermediate through a rolling circle model similar to Ø174 phage. Disease symptoms caused by TYLCV include chlorotic leaf margins, and cupped, thick and rubbery small leaves and significant fruit abscission and overall stunting of plants.

Bacteria and archaea use the clustered regularly interspaced palindromic repeat (CRISPR)/CRISPR associated (Cas) 9, (CRISPR/Cas9), system as a molecular immunity mechanism against invading nucleic acids of conjugative plasmids or phages (Barrangou R. (2013) RNA 4: 267-278; Bikard et al., (2012) Cell Host & Microbe 12: 177-186; Emerson et al., (2013) Archaea 2013: 370871; Marraffini & Sontheimer (2010) Nature Revs. Genetics 11: 181-190; Elmore et al., (2013) RNA Biol. 10: 828-840; Marraffini & Sontheimer (2008) Science 322: 1843-1845). The CRISPR/Cas9 system was used in diverse eukaryotic species for targeted genome editing applications (Cong et al., (2013) Science 339: 819-823; Mali et al., (2013) Science 339: 823-826). The CRISPR/Cas9 system is comprised of the Cas9 endonuclease of *Streptococcus pyogenes* and a synthetic guide RNA (sgRNA) that directs the Cas9 endonuclease to a target sequence complementary to 20 nucleotides preceding the protospacer-associated motif (PAM) (NGG) required for Cas9 activity (Jinek et al., (2012) Science 337: 816-821; Gasiunas et al., (2012) Proc. Nat. Acad. Sci. U.S.A. 109: E2579-2586).

The specificity of the system, and the fact that targeting is determined by the 20-nucleotide sequence of the sgRNA, allows for unprecedented, facile genome engineering. Furthermore, the CRISPR/Cas9 system facilitates multiple, simultaneous targeted modifications (multiplexing) in the genomic targets (Cong et al., (2013) Science 339: 819-823). Targeted DNA mutagenesis using site-specific endonucleases has been used against a variety of mammalian DNA viruses (Schiffer et al., (2012) J. Virol. 86: 8920-8936). Recently, CRISPR/Cas9 system has been used to target different mammalian viruses. For example, it has been used to efficiently eradicate the HIV proviral DNA from the host genome and to prevent the HIV infection (Hu et al., (2014) Proc. Nat. Acad. Sci. U.S.A. 111: 11461-11466). It has also been used to disrupt the hepatitis B virus and to treat the latent infection of Epstein-Barr virus and to engineer the herpes simplex virus (HSV) large DNA genome (Wang & Quake (2014) Proc. Nat. Acad. Sci. U.S.A. 111: 13157-13162; Suenaga et al., (2014) Microbiol. Immunol. 58: 513-522; Zhen et al., (2015) Gene Therapy February 5. doi: 10.1038; Yuen et al., (2014) J. Gen. Virol. 2015 96: 626-636).

As shown by the experimental data of the present disclosure, CRISPR/Cas9 can be advantageously used for in planta viral interference against TYLCV. Different TYLCV ORFs and the IR sequence can be targeted for cleavage and mutagenesis by the CRISPR/Cas9 system. Targeting the TYLCV genome resulted in a significant reduction or attenuation of the disease symptoms. Further, the data reveal the ability of the CRISPR/Cas9 system to target multiple viruses simultaneously. Accordingly, it has been demonstrated that the CRISPR/Cas9 system can be advantageously incorporated into plants and combined with specific viral sgRNA sequences that confer resistance of the plants to TYLCV and other DNA viruses.

Accordingly, one advantageous embodiment of the methods of the disclosure comprises delivering sgRNAs harboring TYLCV sequences via TRV systemic infection into *N. benthamiana* plants over-expressing Cas9 endonuclease (NB-Cas9OE) (generated as taught in Ali et al., (2015) Mol. Plant March 6. S1674-2052, incorporated herein by reference in its entirety).

Figure 1A:
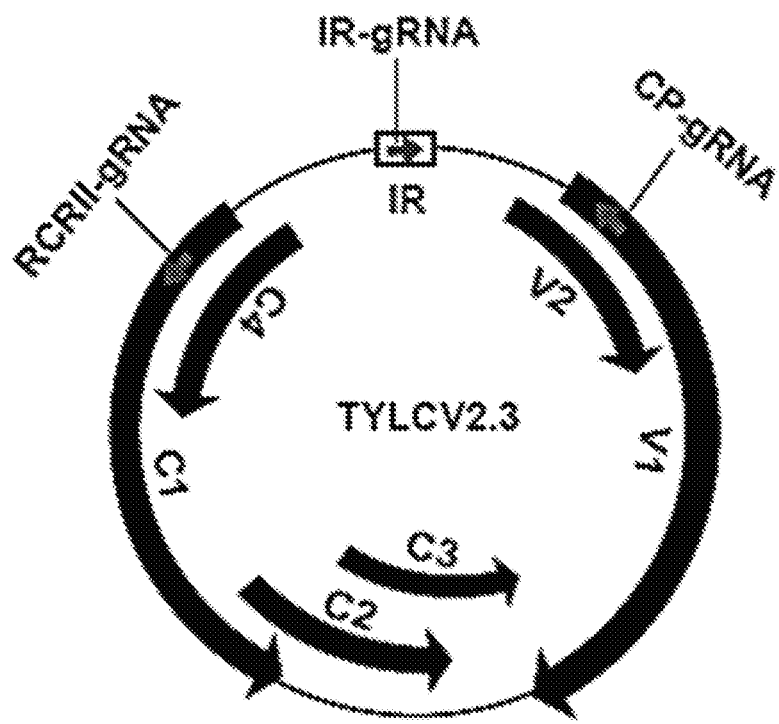
FIG. 1A schematically illustrates the genome of the TYLCV and the sequences of the IR and two ORFs that were targeted with sgRNAs, according to SEQ ID NOs: 117-119, respectively, of the CRISPR/Cas9 system to reduce the infection of a plant by TYLCV.

As shown schematically in FIG. 1A, TYLCV is composed of 6 overlapping ORFs. sgRNAs specific to the IR or ORFs were tested. Genetically-modified recipient NB-Cas9OE plants that accumulated systemically sgRNAs with specificity to TYLCV sequences were challenged with an infectious clone of TYLCV. The TYLCV infectious clone was either infiltrated 7 days post-TRV infiltration or co-infiltrated with the TRV.

Figure 1B:
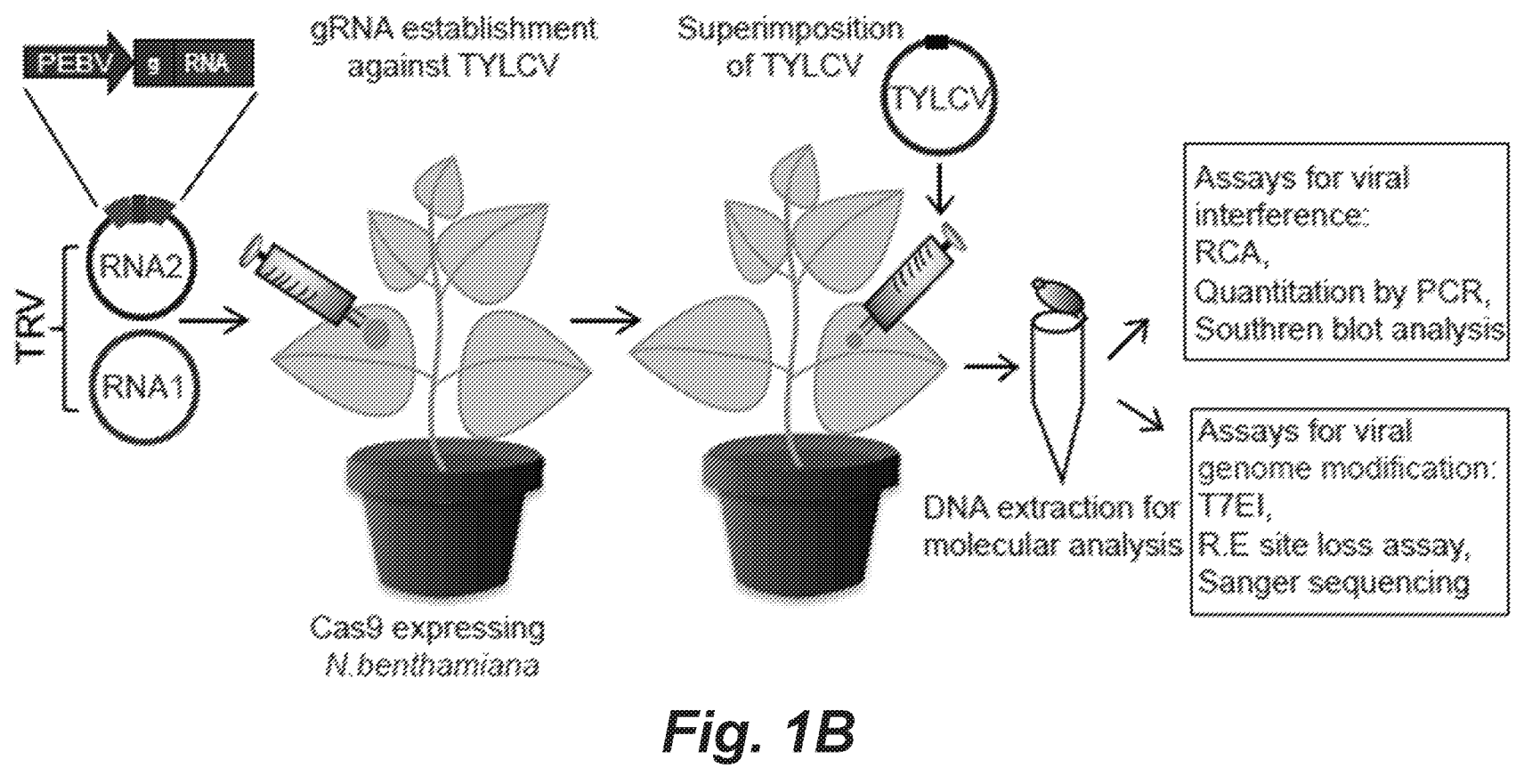

To test whether the CRISPR/Cas9 system interfered with TYLCV, the IR region (the noncoding 314-bp intergenic region (IR) viral element required for viral dsDNA replication) was selected for targeting. The IR is important for replication and transcription of TYLCV. IR-sgRNA, such as having the nucleotide sequence shown in FIG. 1A, was delivered via the TRV system and 7 days post-TRV infiltration; NB-Cas9OE plants were challenged with TYLCV infections clone, as schematically shown in FIG. 1B. Seven days post-agroinfiltration with TYLCV total RNA and DNA were isolated from the plant leaves.

Figure 1C:
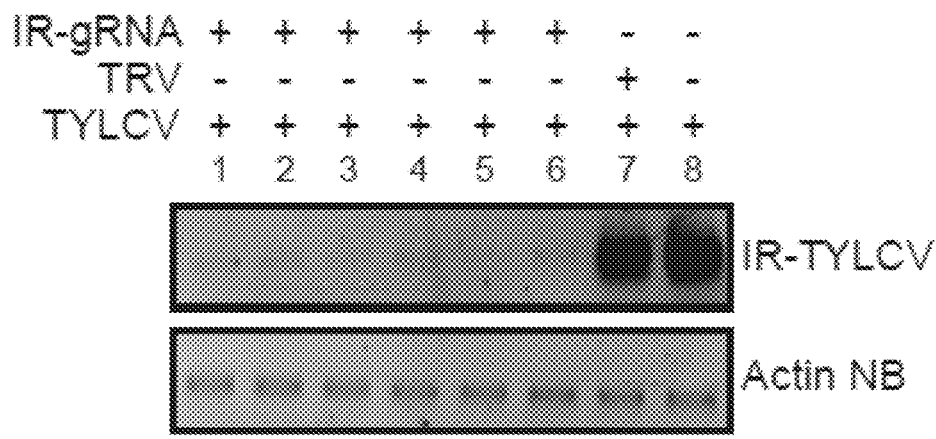
FIG. 1C illustrates the results of a semi-quantitative PCR to determine the TYLCV titer using primers encompassing the IR region.
Figure 1D:
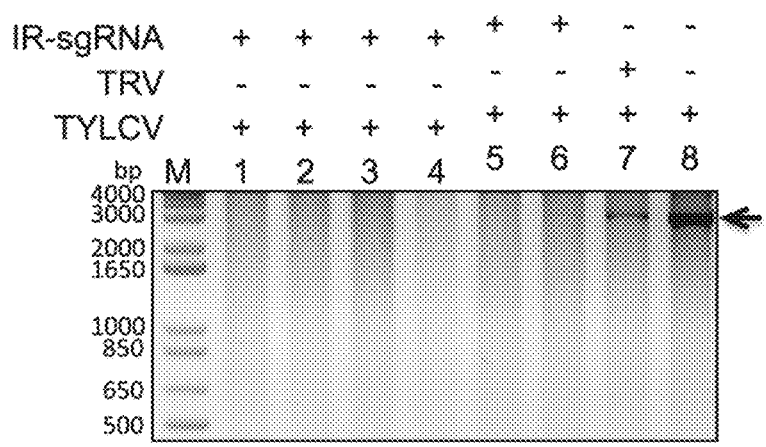
FIG. 1D illustrates the results of an RCA assay to test whether targeting the IR interferes with TYLCV accumulation.

To determine the TYLCV titer, a semi-quantitative PCR was performed using primers encompassing the IR region. Thus, a low titer of TYLCV in the samples co-infiltrated with sgRNA targeting the IR region was compared to the vector controls TRV and TYLCV only. TYLCV replicates through rolling circle amplification using the plant machinery (Bang et al., (2014) Plant Pathology J. 30: 310-315). An RCA assay was performed to test whether targeting the IR interferes with TYLCV accumulation. The data demonstrate that targeting the IR via the CRISPR/Cas9 system interfered with the TYLCV replication (as shown in FIG. 1C).

Figure 1E:
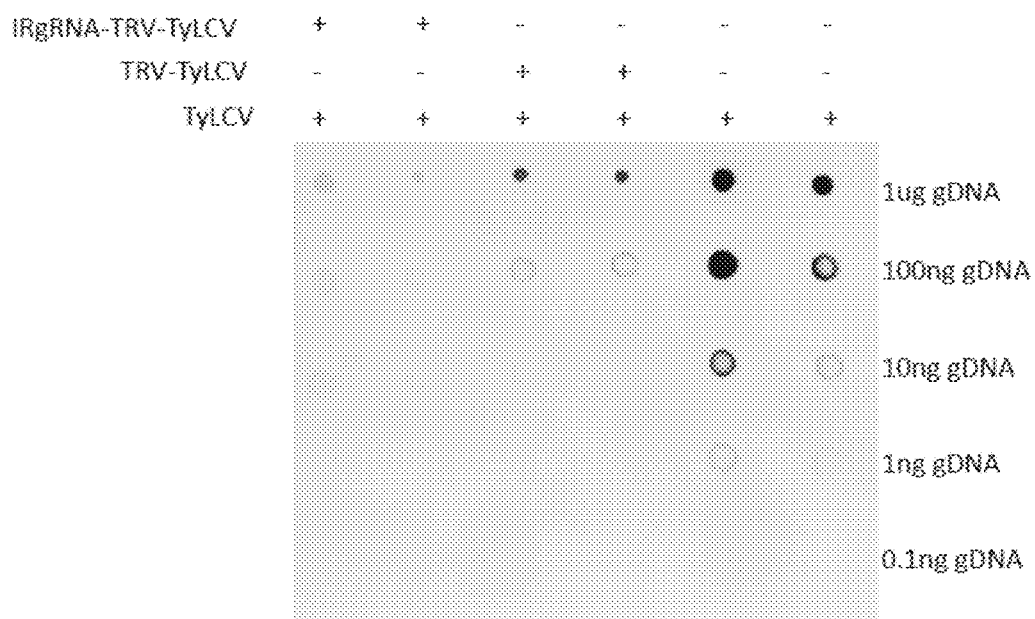
FIG. 1E illustrates the results of a dot blot assay for detecting TYLCV interference.
Figure 1F:
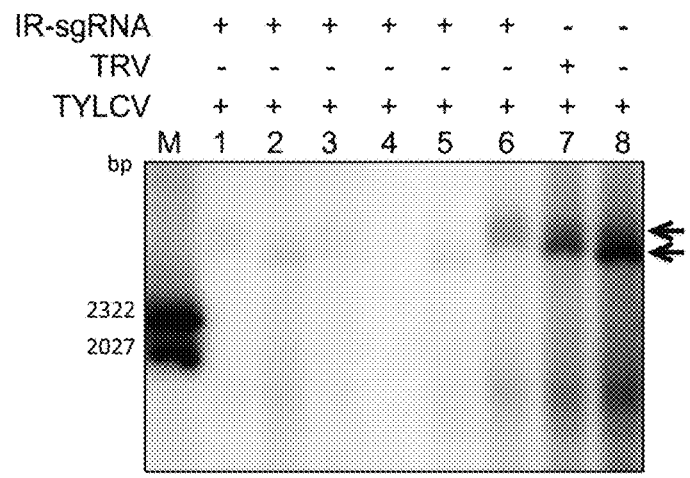
FIG. 1F illustrates the results of Southern blotting assays demonstrating that targeting the IR of the TYLCV led to no detectable accumulation of both ssDNA and dsDNA, compared to empty vector and TYLCV.

Because TYLCV is a single stranded virus and converted to double stranded DNA inside the plant cell nucleus interference with the TYLCV replication by targeting the IR region with CRISPR/Cas9 system would result in no or low accumulation of both ssDNA and dsDNA forms. Therefore, dot blot assays were applied to test the interference with the TYLCV replication. Dot blot results show that TYLCV accumulated at a lower titer in the sgRNA-IR plants compared to vector only negative control and TYLCV-positive control. The dot blot results (FIG. 1E) were confirmed by Southern blotting assays (FIG. 1F). Our results demonstrate that targeting the IR of the TYLCV led to no detectable accumulation of both ssDNA and dsDNA, compared to empty vector and TYLCV.

CRISPR/Cas9 mediates targeted cleavage of TYLCV genome: It was determined whether the attenuated replication of the TYLCV was due to the targeted cleavage or modification of the genome, and not simply due to the binding of the complex and interfering with the replications machinery. Therefore, T7EI and restriction enzyme loss assays were employed to determine the presence and efficiency of the targeted modification within the IR region.

The 20-nucleotide target sequence of the IR region of the TYLCV (SEQ ID NO: 117) as shown in FIG. 1A, contains a recognition sequence (AATATT) for the SspI endonuclease. Genomic DNA was isolated at 7 dpi and a 560 bp fragment was PCR amplified encompassing the IR target sequence and which contained two extra SspI sites. Accordingly, SspI complete digestion of wild fragment produces four fragments with sizes of 53 bp, 92 bp, 189 bp and 216 bp. Moreover, targeted modification at the IR sequence and the subsequent repair via NHEJ will result in a loss of the SspI site within the IR region and a 269 bp resistant band.

Figure 2A:
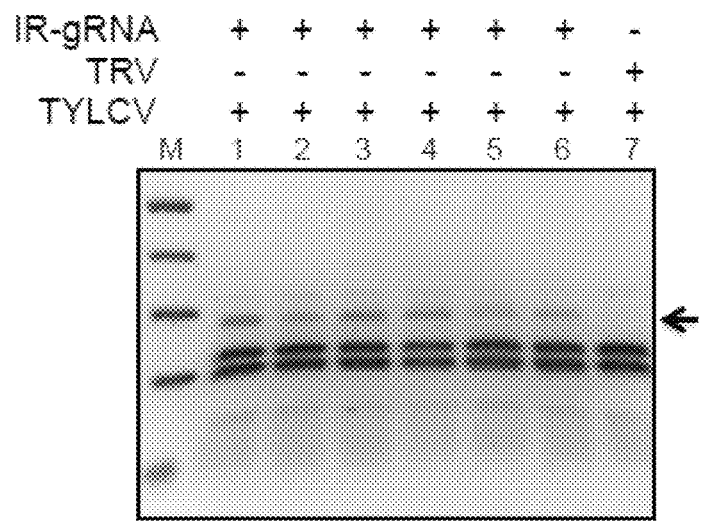
FIG. 2A illustrates a restriction enzyme recognition site loss assay analysis showing the appearance of an SspI-resistant DNA band of 269 bp only in sgRNA-IR samples compared to vector control and TYLCV only, indicating the targeted modification of the IR region by the CRISPR/Cas9 system.

The results demonstrate the appearance of the SspI-resistant DNA band of 269 bp, only in the sgRNA-IR samples compared to vector control and TYLCV alone, indicating the targeted modification of the IR region by the CRISPR/Cas9 system (FIG. 2A).

To validate the presence of indels, the 560 bp PCR amplicons was cloned into pJet 2.1 cloning vector and Sanger sequenced. Alignment of the Sanger sequencing reads indicated that 28% of the clones carry targeted modification within the IR sequence.

Figure 2B:
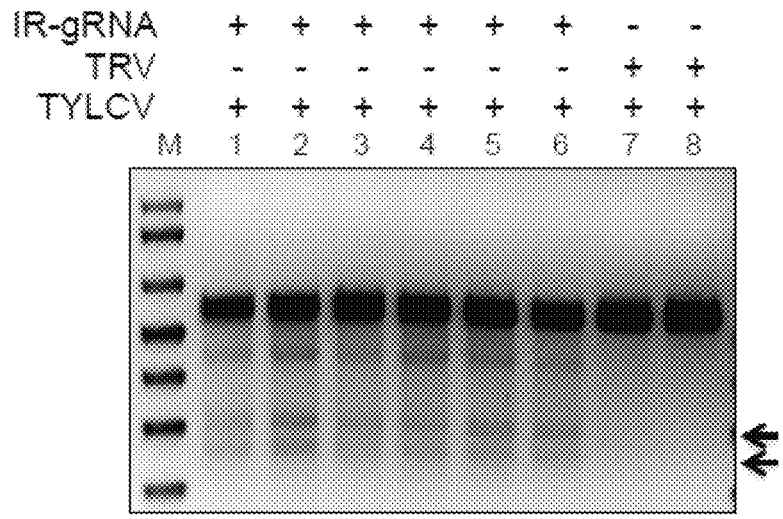
FIG. 2B illustrates that different ORFs can be targeted for modification and used to interfere with TYLCV accumulation.

Furthermore, to test whether other targets in different ORFs mediate interference with TYLCV, as shown in FIG. 2B, two other sgRNAs targeting the CP and Rep ORFs were designed. The T7EI and/or restriction site loss assays and Sanger sequencing indicated that different ORFs besides just the IR can be targeted for modification and used to interfere with TYLCV accumulation (FIGS. 2C and 2D). Further, the T7EI and restriction loss assays were corroborated using RCA and Southern blotting.

CRISPR/Cas9 system mediates specific targeting and interference with the TYLCV genome: It was determined whether the CRISPR/Cas9-mediated specifically interferes with the TYLCV. The IR regions of most of the geminiviruses are conserved within each specific type of virus (Yang et al., (2004) Phytopathology 94: 490-496). To confirm that the IR-sgRNA was targeting only TYLCV IR region and interfering specifically with TYLCV genome replication, another mono-partite geminivirus, the Beet Curly Top Virus (BCTV) strain Logon was co-infiltrated with TYLCV-IR-sgRNA (FIG. 3A). The modification of the IR sequence of both TYLCV and BCTV was tested by restriction enzyme loss and T7EI assays (FIGS. 3B and 3C). The results confirmed that TYLCV-IR-sgRNA specifically targeted TYLCV genome, but not Logon genome. Conversely, it was also confirmed that BCTV-IR-sgRNA targeted the BCTV genome but not TYLCV genome (FIGS. 4A-4C).

CRISPR/Cas9 system attenuates or represses the TYLCV symptoms: The interference with TYLCV replication by the CRISPR/Cas9 machinery would lead to reduced or cleared TYLCV symptoms reminiscent of the natural immunity in bacteria against phages. Accordingly, the TYLCV symptoms were assessed and evaluated in NB-Cas9OE plants challenged with TYLCV infectious clone. Three groups of NB-Cas9OE plants expressing the sgRNAs specific for the IR, CP and Rep regions were challenged with the infectious clone.

Figure 5A:
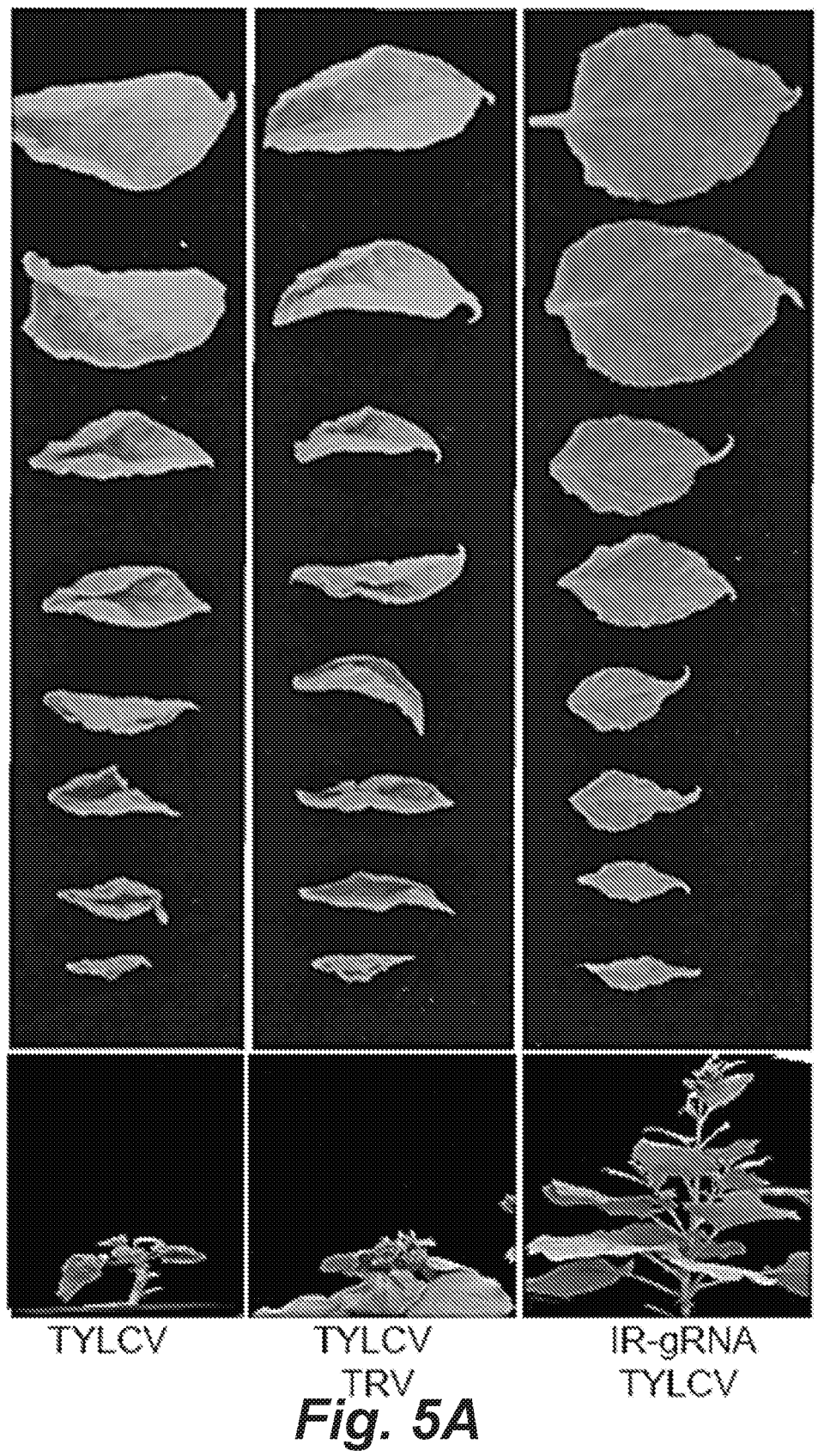
FIG. 5A illustrates that NB-Cas9OE plants expressing sgRNA targeting the IR region showed significantly reduced TYLCV symptoms compared with controls.
Figure 5B:
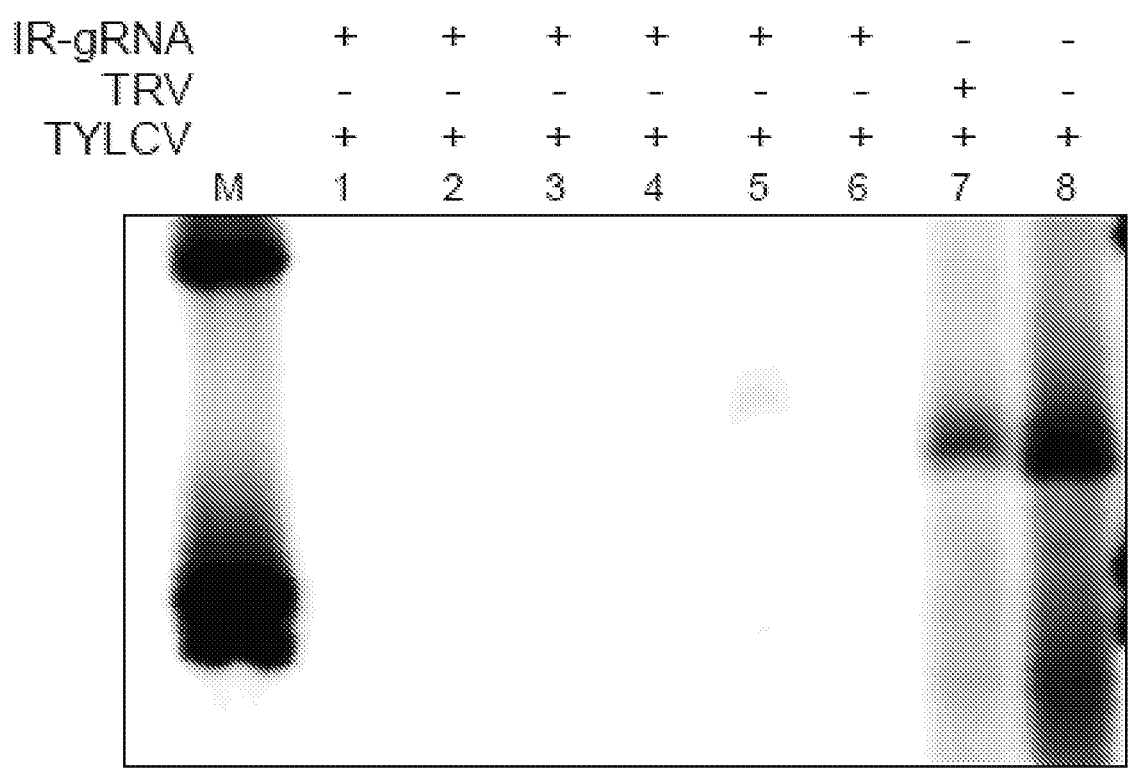
FIG. 5B illustrates the results of a Southern blot analysis confirming the absence or reduction of TYLCV genome in samples of the IR-sgRNA infiltrated plants. The results confirmed the absence, or significant reduction of, TYLCV in the IR-sgRNA targeted plants compared with the vector control.

NB-Cas9OE plants expressing sgRNA targeting the IR region showed significantly reduced TYLCV symptoms compared with positive and negative controls. Moreover, NB-Cas9OE plants expressing sgRNA targeting CP or Rep ORFs showed reductions of TYLCV symptoms but not as significant as with the sgRNA targeting the IR sequence. Southern blotting confirmed the absence, or significant reduction, of TYLCV in the IR-sgRNA targeted plants compared with the vector control (FIGS. 5A and 5B).

The phenotypic data of the TYLCV symptoms corroborated the molecular analysis results that showed significant reduction of the viral genome when the IR region was targeted for cleavage. In a second set of experiments, it was tested whether targeting more than one sequence of the TYLCV genome would lead to further elevated and effective reduction of TYLCV symptoms. Therefore, sgRNAs targeting the CP and IR regions were co-expressed as well as sgRNAs targeting the CP and Rep proteins. The data demonstrate that targeting two different sequences did not have an additive effect on the reduction of TYLCV symptoms or the accumulation of the virus genome. Similarly, the co-expression of CP and RCR sgRNAs resulted in a reduction of TYLCV symptoms at levels similar to the expression of either CP or RCR single sgRNA.

All viruses possess at least one RNA silencing suppressor to counteract the host defense and produce successful infections (Pumplin & Voinnet (2013) Nature Revs. Microbiology 11: 745-760). The CRISPR/Cas9 system provides molecular immunity mechanism to bacterial and archaeal species to fend off viral infections (Doudna & Charpentier (2014) Science 346: 1258096). The data of the disclosure demonstrate the advantageous use of the CRISPR/Cas9 system to function as a heterogeneous molecular immunity mechanism in plants specifically directed against invading DNA viruses.

Recently, a method for the delivery of sgRNA molecules systemically into the Cas9-OE *N. benthamiana* was described (Ali et al., (2015) Mol. Plant March 6. S1674-2052 incorporated herein by reference in its entirety, including all supplemental material therein). This approach was employed to test whether the CRISPR/Cas9 system can be used for interference against TYLCV. Accordingly, sgRNA molecules were systemically delivered via the TRV system and assessed for the interference of the (co-infiltrated) TYLCV replication and accumulation and symptoms development. Extensive molecular analysis has shown that co-infiltration of TRV harboring sgRNAs targeting specific sequences in the TYLCV with the TYLCV virus led to significant repression of viral replication and accumulation. Since the binding of the CRISPR/Cas9 system to the IR region can attenuate the virus replication, the presence and efficiency of genomic modification at the IR region was investigated and significant levels of genomic modification were found, indicating the usefulness of the CRISPR/Cas9 system to target viral genomes.

Whether Cas9 can target different TYLCV ORFs for cleavage was then tested. sgRNAs targeting the ORFs of CP and RCR were designed, constructed and systemically delivered. The data demonstrate that CRISPR/Cas9 is capable of targeting regions of the TYLVC genome in addition to the IR region such as the ORFs encoding the CP, RCR. This result indicated the advantageous use of the CRISPR/Cas9 system for targeted interference of plant viral genomes.

Targeted cleavage of viral genomes may lead to interference with its replication, systemic infection and development of viral symptoms. Whether targeting the IR region, known to be essential for viral replication and transcription, would affect the viral replication and accumulation was tested. RCA, semi-quantitative PCR, and Southern blotting assays were employed to indicate that targeting the IR region led to significant reductions of the viral replication and accumulation compared to the vector only negative control and positive control. Therefore, the data suggest the advantageous use of the CRISPR/Cas9 system for interference with plant DNA viruses. Whether targeting different ORFs simultaneously would lead to further reduction of the viral replication and accumulation by targeting the CP and Rep ORFs was investigated. The data demonstrate that targeting CP and Rep ORFs resulted in reductions of viral replication and accumulation at levels similar to those when a single sgRNA for either CP or Rep was used, i.e. there was no cumulative effect from combining the two sgRNAs targeting individual ORFs. Similarly, simultaneous targeting of the IR and CP sequences by co-expression of sgRNAs targeting their sequences did not have an additive effect and led to reduction of viral accumulation and symptoms at levels similar to using single sgRNA targeting the sequence.

Targeting CP and Rep ORFs resulted in attenuated symptoms but at levels lower than found with that of the IR target. Not wishing to be bound by any one theory, it is possible that binding of the CRISPR/Cas9 system to the IR region could have a combined effect of modification and repression of replication and transcription by occupying key sequences for these processes. Notably, the IR region is important for viral replication and transcription and manipulations of this region may have significant consequences compared to other sequences in other ORFs.

An advantageous criterion for in planta viral interference is specificity against targeted viral strains. Therefore, the ability of the CRISPR/Cas9-mediated viral interference system according to the disclosure to specifically target a particular virus by co-agroinfiltration of the two viral strains TYLCV and Worlond was tested. The results showed that when sgRNA targeting TYLCV sequences was used, only the TYLCV genome was modified, and when sgRNA-targeting Worlond was used, only the Worlond genome sequence was modified, indicating the system target virus specificity.

The ability of the systems and methods of the disclosure to exert specificity is particularly advantageous in targeting newly evolved viral variants. For example, while not wishing to be limiting, resistance based on the plant host could place selection pressure on the virus and lead to adaptation and a successful infection by the generation of the variants with better adaptation, e.g. by changing the PAM tri-nucleotide sequence and abrogating the recognition of the target sequence by the CRISPR/Cas9 system. That the emergence of TYLCV recombinant variants can overcome resistance has been reported in Ty-I resistant plants (Verlaan et al., (2013) PLoS Genetics 9:e1003399). Thus, since the CRSIPR/cas9 system of the disclosure targets the virus DNA for destruction; DNA repair could lead to the generation of a viral variant with a different PAM sequence, thereby escaping from the activity of the CRISPR/Cas9 system. Since certain DNA sequences are central to viral replication, e.g. the IR region, mutagenesis of this sequence could lead to a significant reduction of viral replication.

To maintain the replication of a new virus variant, the target sequence must mutate to escape the recognition of the CRISPR/Cas9 system and simultaneously the key replication machinery enzymes that bind to such sequences must mutate to recognize the new sequence. Furthermore, simultaneously targeting two viral sequences for cleavage will lead to the destruction of the viral genome and reduce the likelihood of DNA repair and generation of infectious virus variant. Emerging variants can, therefore, be combated through the design and application of sgRNA molecules with specificity to novel variant sequences.

Although the data did not show any additive effect on the accumulation of the TYLCV genome or symptoms development, this might be due to the nature of the carrier TRV infection resulting in the two sgRNAs not being made in single cells and available to cleave the TYLCV at more than one site simultaneously. It is contemplated, however, to be within the scope of the disclosure for the generation of TYLCV host plants stably expressing Cas9 and multiple sgRNAs that can exhibit additive effects and elevated resistance to TYLCV.

It was also tested whether the methods and systems of the disclosure can simultaneously target a plurality of viral strains. This was achieved in one demonstration by co-infiltration of sgRNAs targeting TYLCV and the Beet Curly Top Virus (strain Worlond). The data suggest that it is possible to simultaneously target more than one viral strain. This approach can advantageously be used to engineer plants resistant to multiple DNA viruses or viral strains. Thus, it has been recently reported that it is possible to express several sgRNAs simultaneously (Xie et al., (2015) Proc. Nat. Acad. Sci. U.S.A. 112:3570-3575). This system can be used to express sgRNAs with specificity to multiple DNA viruses. The application of the CRISPR/Cas9-mediated viral interference technology provides platform to develop crop cultivars with superior resistance to single or multiple viruses.

The efficiency of the CRISPR/Cas9 machinery was investigated for targeting different coding and non-coding sequences of geminivirus genomes and assessed the rate of indel formation in coding and non-coding regions of these viruses. Whether virus variants were generated and whether the generation of these variants would eventually enable the virus to evade the CRISPR/Cas9 machinery was also examined. To investigate the versatility of the CRISPR/Cas9 system in conferring interference against different geminiviruses, the interference activity against Cotton Leaf Curl Kokhran Virus (CLCuKoV) was investigated, which required the helper Cotton Leaf Curl Multan Betasatellite (CLCuM☐) for disease symptom development. sgRNAs targeting the coding and non-coding regions of CLCuKoV individually were tested to determine their efficacy in directing the Cas9 endonuclease to the viral genome and establishing interference. The data show that sgRNAs targeting the coding regions of the CP and RCRIII ORFs mediated high levels of interference, as evidenced by the indel mutation detection assays, which was subsequently confirmed by Sanger sequencing. By contrast, indel modifications were not detected in the IR via the T7EI and restriction site loss assays using an sgRNA targeting the IR of the CLCuKoV or variant sgRNAs. These results suggest that either the sgRNA was inactive and incapable of directing the Cas9 endonuclease to the target virus sequence or that the targeting occurred but the DSBs were not repaired via NHEJ and the cleaved virus sequences were subsequently degraded or the repaired variants were incapable of replication.

Coding and non-coding sequences of other bipartite viruses could be targeted by CRISPR/Cas9, with subsequent NHEJ resulting in indel modifications. The bipartite MeMV (DNA-A and DNA-B genomes) and designed sgRNAs targeting the IR and ORFs (CP and RCRIII, respectively) were targeted. It was found that sgRNAs targeting the coding and noncoding sequences were capable of targeting and interfering with subsequent NHEJ repair, as revealed by the T7EI and restriction site loss assays and Sanger sequencing. Therefore, the CRISPR/Cas9 system can interfere with bipartite viruses (MeMV) and target the IR, with subsequent NHEJ repair. Notably, differential CRISPR/Cas9-based indel formation in human viruses was also recently reported (Baltes et al., Nat. Plants 1, 15145 (2015); Ji et al., Nat. Plants 1, 15144 (2015); Mansoor et al., Arch. Virol. 148, 1969-1986 (2003).

Variable efficiencies of targeting the IR and the subsequent repair of DSBs were observed and it was attempted to determine whether targeting the IRs of different strains of the same geminivirus would be similar or would vary. To investigate this, two different strains of TYLCV, i.e., TYLCV2.3 and the severe strain TYLCVSV were used. Examination of the designed sgRNAs, including the invariant conserved nonanucleotide target sequence, revealed the absence of indels at the IR of TYLCSV. However, the same sgRNA, as well as another authentic sgRNA targeting the TYLCV2.3 IR, were able to target TYLCV2.3, and the IR was subsequently repaired by NHEJ, as evidenced by the presence of indel modifications in the T7EI and restriction site loss assays. Consistent with the previous results, all sgRNAs targeting the ORF (CP and RCRII) sequences were highly efficient in targeting all virus strains, with subsequent repair via NHEJ, as evidenced by the T7EI assays and Sanger sequencing.

The inability to detect any indel modifications in viral genomes from plants carrying sgRNAs targeting the IRs of TYLCVSV and CLCuKoV prompted further investigation. Such inability could involve: 1) the inability of the sgRNA to target the Cas9 protein to the IR sequences of CLCuKoV and TYLCVSV; 2) the inability of the NHEJ repair machinery to repair DSBs, ultimately leading to degradation of the cleaved IR sequences of these two viruses; or 3) the IR repaired variants of individual genomes were unable to replicate and were ultimately degraded. To determine which of these possibilities is in play, the interference activities was investigated by measuring the accumulation of the genomes of these two viruses. Interestingly, the sgRNAs targeting the IRs of CLCuKoV and TYLCVSV were capable of directing the CRISPR/Cas9 machinery to the IR, thereby interfering with viral replication, ultimately resulting in a significant reduction in viral genome levels. Therefore, the findings indicate that the IR sgRNA can target the viral genome, but the subsequent repair of the DSBs via NHEJ is likely to generate viral variants inefficient in viral replication. This prompted us to sequence numerous amplicons to determine whether indel production or other types of modifications could have taken place. Sanger sequencing of the IR amplicons revealed the presence of a few IR sequences with large deletions ranging from 61-360 bp, indicating the inefficiency of NHEJ repair.

The data reveal that the targeting and subsequent modification of coding regions via NHEJ repair are quite efficient and universal among the geminiviruses examined. However, sgRNAs targeting the IR are capable of interference, but the subsequent repair process results in variants inefficient in replication. Moreover, it is likely that amplicons with long deletions would be incapable of replication and systemic infection. Since efficient NHEJ repair was observed in the coding sequences of the CP and RCRIII, it was investigated whether these repaired sequences with indels, which constitute different protein variants, can replicate and survive, and could therefore move systemically throughout the plant. This hypothesis was investigated by applying CRISPR/Cas9 machinery targeting the coding sequences of the virus. Subsequently, the presence of indels by mutation detection assays was confirmed, and sap was used as a source of the virus variants generated by NHEJ repair to inoculate WT *N. benthamiana* plants. The presence of these variants was then assayed for in the systemic leaves of WT *N. benthamiana* plants. Virus variants were detected in the systemic leaves of WT *N. benthamiana* plants, indicating the capability of these variants to replicate and systemically move throughout the plant. By contrast, a similar set of experiments was performed using the sap from CRISPR/Cas9 machinery targeted to the IR. Virus variants with modifications in the IR were not detected, corroborating the previous results and indicating that the NHEJ repaired variants are inefficient in replication. Notably, the ability of virus variants to replicate and subsequently dodge CRISPR/Cas9 was recently observed in HIV-1.

The findings provide important insights into the potential use of the CRISPR/Cas9 system for virus interference. Since NHEJ repair of the coding regions of different geminiviruses is quite efficient, leading to the generation of different viral variants capable of replication and systemic infection, it may be possible to generate viral variants that escape the CRISPR/Cas9 machinery. The selection and replication of these repaired variants would favor the more fit variants for virus survival. Since these viral variants could have variable replication efficiencies, it is expected that the variants with more proficient replication would predominate over those with less proficient replication. It also remains to be determined whether targeting certain genomic regions would increase the recombination frequencies under natural field conditions where mixed infections predominate.

The short genomes of viruses contain highly specialized, specific sequences required for specific functions including viral replication, evading host defense systems, and host infection. When designing interference strategies against viruses and coping with putative viral escape, the main focus is on the sequences that provide better interference when used for targeted interference. Similarly, given the considerable heterogeneity and recombination ability of geminiviruses and the ability of CRISPR/Cas9-induced variants for replication and systemic movement, it would be conceivable to devise strategies where the CRISPR/Cas9 system targets the noncoding region (three nucleotides before the PAM) to inhibit or prevent the replication of the virus by mutating the essential parts of geminiviruses. Alternatively, targeting multiple regions of the virus genome simultaneously would abrogate the ability of the virus to use the NHEJ repair system, and these cleaved molecules would ultimately be degraded. Because the IR is critical for binding and replication initiation 42, targeting this region by a catalytically inactive Cas9 would be expected to abrogate viral replication and subsequently lead to virus interference. In conclusion, the study highlights important aspects to consider when developing CRISPR/Cas9-based strategies for durable virus interference and resistance, thereby improving agricultural productivity.

One aspect of the disclosure encompasses embodiments of a genetically modified plant resistant to at least one pathogenic geminivirus species, said plant comprising a heterologous CRISPR/Cas9 system and at least one heterologous nucleotide sequence that is capable of hybridizing to a nucleotide sequence of the pathogenic virus under stringent conditions, or to a complement thereof, and that directs inactivation of the pathogenic virus species or plurality of viral species by the CRISPR/Cas9 system.

In some embodiments of this aspect of the disclosure, the at least one heterologous nucleotide sequence can be inserted into a chromosome of the plant, is an extrachromosomal element, or is inserted in a vector.

In some embodiments of this aspect of the disclosure, the pathogenic virus is of the geminiviridae.

In some embodiments of this aspect of the disclosure, the pathogenic virus can be of the geminiviridae genus *Becurtovirus, Begomovirus, Curtovirus, Eragrovirus, Mastrevirus, Topocuvirus* or *Turncurtovirus*.

In some embodiments of this aspect of the disclosure, the pathogenic virus can be selected from the group consisting of: Beet Curly Top Iran virus, Spinach Severe Curly Top Virus, Bean golden mosaic virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV).

In some embodiments of this aspect of the disclosure, the plant is a tobacco plant or a tomato plant.

In some embodiments of this aspect of the disclosure, the at least one heterologous nucleotide sequence is capable of hybridizing under stringent conditions to a nucleotide sequence of the pathogenic virus, or to a complement thereof, and wherein the nucleotide sequence of the pathogenic virus is an Intergenic Region (IR) or an Open Reading Frame (ORF) thereof.

In some embodiments of this aspect of the disclosure, the at least one heterologous nucleotide sequence is capable of hybridizing under stringent conditions to a nucleotide sequence of an Intergenic Region (IR) of the pathogenic virus, or to a complement thereof.

In some embodiments of this aspect of the disclosure, the at least one heterologous nucleotide sequence is capable of hybridizing under stringent conditions to a nucleotide sequence of an Intergenic Region (IR) of the Tomato Yellow Leaf Curl Virus (TYLCV), or to a complement thereof.

In some embodiments of this aspect of the disclosure, the at least one second heterologous nucleotide sequence can have the nucleic acid sequence 5'-GGCCATCCGTATAATATTAC-3' (SEQ ID NO: 75).

Accordingly this aspect of the disclosure encompasses embodiments of a genetically modified tobacco plant or tomato plant resistant to at least one pathogenic geminivirus species selected from the group consisting of: Beet Curly Top Iran Virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV), said plant comprising a heterologous CRISPR/Cas9 system and at least one heterologous nucleotide sequence that is capable of hybridizing to an Intergenic Region (IR) nucleotide sequence of the pathogenic virus under stringent conditions, or to a complement thereof, and that directs inactivation of the pathogenic virus species or plurality of viral species by the CRISPR/Cas9 system, wherein the at least one heterologous nucleotide sequence is inserted into a chromosome of the plant, is an extrachromosomal element, or is inserted in a vector.

In some embodiments of this aspect of the disclosure, the at least one heterologous nucleotide sequence is capable of hybridizing under stringent conditions to a nucleotide sequence of an Intergenic Region (IR) of the Tomato Yellow Leaf Curl Virus (TYLCV), or to a complement thereof and has the nucleic acid sequence 5'-GGCCATCCGTATAATATTAC-3' (SEQ ID NO: 75).

Another aspect of the disclosure encompasses embodiments of a method of generating a genetically modified plant resistant to a virus pathogen, the method comprising the steps of: (a) obtaining a plant susceptible to a pathogenic virus, wherein said plant is genetically modified to express a heterologous CRISPR/Cas9 system; and (b) genetically modifying said plant to include at least one heterologous nucleotide sequence capable of hybridizing under stringent conditions to a nucleotide sequence of the pathogenic virus, or to a complement thereof, and wherein the at least one heterologous nucleotide sequence can direct inactivation of the virus pathogen by the CRISPR/Cas9 system.

In some embodiments of this aspect of the disclosure, the step (b) comprises delivering the at least one heterologous nucleotide sequence to a population of cells of the plant by transfection with viral vector, by a mechanical method, or by genetically modifying an isolated plant cell and generating the plant therefrom.

In some embodiments of this aspect of the disclosure, the method can further comprise the step of cultivating the genetically modified plant resistant to a virus pathogen to generate a population of said plants, wherein said progeny are reproduced sexually or asexually.

In some embodiments of this aspect of the disclosure, the pathogenic virus can be of the genus geminiviridae.

In some embodiments of this aspect of the disclosure, the pathogenic virus can be of the geminiviridae genus *Becurtovirus, Begomovirus, Curtovirus, Eragrovirus, Mastrevirus, Topocuvirus* or *Turncurtovirus*.

In some embodiments of this aspect of the disclosure, the pathogenic virus can be selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV).

In some embodiments of this aspect of the disclosure, the pathogenic virus is Tomato Yellow Leaf Curl Virus (TYLCV).

In some embodiments of this aspect of the disclosure, the plant can be a tobacco plant or a tomato plant.

In some embodiments of this aspect of the disclosure, the heterologous nucleotide sequence is capable of hybridizing under stringent conditions to a nucleotide sequence of an Intergenic Region (IR) or an Open Reading Frame (ORF) of the pathogenic virus, or to a complement thereof.

In some embodiments of this aspect of the disclosure, the heterologous nucleotide sequence is capable of hybridizing under stringent conditions to a nucleotide sequence of an Intergenic Region (IR) of the pathogenic virus, or to a complement thereof.

In some embodiments of this aspect of the disclosure, the heterologous nucleotide sequence is capable of hybridizing under stringent conditions to a nucleotide sequence of an Intergenic Region (IR) of the Tomato Yellow Leaf Curl Virus (TYLCV), or to a complement thereof.

In some embodiments of this aspect of the disclosure, the heterologous nucleotide sequence has the nucleic acid sequence 5'-GGCCATCCGTATAAT<u>AT</u>TAC-3' (SEQ ID NO: 75).

Accordingly, this aspect of the disclosure encompasses embodiments of a method of generating a genetically modified plant resistant to a virus pathogen, the method comprising the steps of: (a) obtaining a plant susceptible to a pathogenic geminivirus of the geminiviridae genus *Becurtovirus, Begomovirus, Curtovirus, Eragrovirus, Mastrevirus, Topocuvirus* or *Turncurtovirus*, and wherein said plant is genetically modified to express a heterologous CRISPR/Cas9 system; (b) genetically modifying said plant to have at least one heterologous nucleotide sequence capable of hybridizing under stringent conditions to a nucleotide sequence, or to a complement thereof, of an Intergenic Region (IR) or an Open Reading Frame (ORF) of the pathogenic virus, and wherein said at least one heterologous nucleotide sequence can direct cleavage of the virus pathogen by the CRISPR/Cas9 system, wherein step (b) comprises delivering the at least one heterologous nucleotide sequence to a population of cells of the plant by transfection with viral vector, by a mechanical method, or by genetically modifying an isolated plant cell and generating the plant therefrom; and (c) cultivating the genetically modified plant resistant to a virus pathogen to generate a population of progenies of said plants, wherein said progeny are reproduced sexually or asexually.

In some embodiments of this aspect of the disclosure, pathogenic virus is selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV), and wherein the plant is a tobacco plant or a tomato plant.

In some embodiments of this aspect of the disclosure, pathogenic virus is Tomato Yellow Leaf Curl Virus (TYLCV), the heterologous nucleotide sequence is capable of hybridizing under stringent conditions to a nucleotide sequence of an Intergenic Region (IR) of the Tomato Yellow Leaf Curl Virus (TYLCV), or to a complement thereof In some embodiments of this aspect of the disclosure, heterologous nucleotide sequence has the nucleic acid sequence 5'-GGCCATCCGTATAAT<u>AT</u>TAC-3' (SEQ ID NO: 75).

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

Vector construction: To clone sgRNAs targeting TYLCV genome in TRV RNA2 vector, a PCR based restriction ligation procedure was used. A fragment containing the 20-nucleotide target sequence, an 84 bp Cas9 binding loop of sgRNA followed by a repeat of 7 T nucleotides as terminator was amplified by PCR. A forward primer designed to contain XbaI recognition site, 20-nucleotide target sequence followed by 23 nucleotides of the Cas9 binding sgRNA scaffold was used with a reverse primer containing XmaI recognition site to amplify a 116 bp PCR fragment, primer sequences provided in Table 1.

TABLE 1

| Primers Name | Sequence (5'→3') | Usage |
| --- | --- | --- |
| TYLCV2.3-IR-T-F | AATTGGGAAAGTGCTTCCTCT (SEQ ID NO: 43) | Semi-qPCR, to amplify TYLCV IR flanking region, to make probe for southern, detection TYLCV by PCR |
| TYLCV2.3-IR-T-R | ATAGTCACGGGCCCTTACAACA (SEQ ID NO: 44) | |
| TYLCV-IR-T1 | CGAGTCTAGAGGCCATCCGTATA ATATTACGTTTTAGAGCTAGAAAT AGCAAG (SEQ ID NO: 45) | To clone TYLCV IR-sgRNA |
| SPDK-sgRNA-R | ACATGCCCGGgAAAAAAAGCACC GACTCGG (SEQ ID NO: 46) | To clone all sgRNA |
| NB-ACTIN1-RT-F | TGAAGATCCTCACAGAGCGTGG (SEQ ID NO: 47) | RT-PCR normalization control |
| NB-ACTIN1QRT-LIU-R | TTGTATGTGGTCTCGTGGATTC (SEQ ID NO: 48) | |
| TYLCV-CP-T1 | CGAGTCTAGAGCTTCGGCGAAC CTTCGAGACGTTTTAGAGCTAGA AATAGCAAG (SEQ ID NO: 49) | To clone TYLCV CP-sgRNA |

TABLE 1-continued

| Primers Name | Sequence (5'→3') | Usage |
|---|---|---|
| TYLCV-RCRIII-T1 | CGAGTCTAGAGAAGCGATGTCAA ATCCTATAGTTTTAGAGCTAGAAA TAGCAAG (SEQ ID NO: 50) | To clone TYLCV RCRIII-sgRNA |
| TRV1-RELICASE-RT-F | CTACTGGGAGAGCAGCAACC (SEQ ID NO: 51) | For detection of TRV-RNA1 systemic movement |
| TRV1-REPLICASE-RT-R | CTGAGCGCAAAAGTACACCA (SEQ ID NO: 52) | |
| TRV2-CP-RT-F | TTGGGTGGAATCAGTTTCGT (SEQ ID NO: 53) | For detection of TRV-RNA2 systemic movement |
| TRV2-CP-RT-R | TCTTCCAAAGTCGAGCCAGT (SEQ ID NO: 54) | |
| WOR-L1-T1/2-F | TGCTTCAGCTGCATTACCTG (SEQ ID NO: 55) | For PCR flanking Worland RCRII target |
| WOR-L1-T1/2-R | ATGGCCCTGGAGGTATATAAG (SEQ ID NO: 56) | |
| WOR-RCRII-T | CGAGTCTAGAGCTTTGAATTGGA TGAGGGCGGTTTTAGAGCTAGAA ATAGCAAG (SEQ ID NO: 57) | To clone LOGON RCRII-sgRNA |
| TYLCV2.3-CP-T1/2-F | TTCTTCACGGTTGCGGTACT (SEQ ID NO: 58) | For PCR flanking TYLCV CP target |
| TYLCV2.3-CP-T1/2-R | GAGCTTTGGACCCTGAATTG (SEQ ID NO: 59) | |
| TYLCV2.3-REP-T1/2-F | GAGCTTTGGACCCTGAATTG (SEQ ID NO: 60) | For PCR flanking TYLCV RCRIII target |
| TYLCV2.3-REP-T1/2-R | TTGGAGCGTGATGATTTTGA (SEQ ID NO: 61) | |

The 116 bp PCR fragment of the sgRNA of each target was cloned into the TRV RNA2 vector under the PEBV promoter using XbaI and XmaI restriction enzymes. Sanger sequencing was used to confirm clone sequences.

Example 2

Agroinfiltration: Binary constructs, including TRV RNA2 harboring the sgRNA, TRV RNA1, and TYLCSV, MeMV DNA-A, MeMV DNA-B, CLCuKoV, and CLCuMB infectious clones, were individually transformed into *Agrobacterium tumefaciens* strain GV3103 by electroporation. Transformed single colonies were grown overnight in selective medium, pelleted, and re-suspended. The bacterial cultures were mixed prior to infiltration and diluted to OD600~0.05 (for the infectious clones of DNA viruses) or 0.1 (for RNA1 and RNA2) in infiltration medium (10 mM MES [pH 5.7], 10 mM $CaCl_2$), and 200 µM acetosyringone). The cultures were incubated at ambient temperature in the dark for 4-8 h. Mixed bacterial cultures were infiltrated into the 3- to 4-week-old leaves of *N. benthamiana* Cas9-OE plants using a 1 mL needleless syringe. Leaf disc samples were collected from inoculated plants, and systemic leaves at 15 and 21 dpi and were subjected to various molecular analyses to determine the presence of targeted modifications of the viral sequences.

Bacterial cultures mix was infiltrated into the lower side of 3 to 4 weeks-old leaves of *N. benthamiana* Cas9 overexpression plants using a needleless 2 mL syringe. Samples of leaf discs were collected from inoculated and systemic leaves 5, 10, 15 and 30 days post-infiltration and subjected to molecular analyses to determine viral load and targeted modification of the viral sequence.

Example 3

Semi-quantitative RT-PCR: Genomic DNA was extracted from plant samples as previously described in Ali Z, et al., (2015) Mol. Plant March 6. S1674-2052, incorporated herein by reference in its entirety). DNA was quantified using Nano Drop and adjusted to 50 ng/µL. A primer set was used to amplify a 560 bp fragment from the TYLCV genome. PCR of 23-25 cycles was performed using Phusion polymerase (New England Biolab). A primer set to amplify the genomic DNA corresponding to *N benthamiana* actin was used as normalization control.

Example 4

Mutation detection assay using restriction enzyme resistance: To determine the presence of targeted modification in the TYLCV genome via CRISPR/Cas9 system the restriction enzyme resistance assay was employed to the PCR products encompassing the target sequence. Thus, genomic DNA was isolated from samples collected after 7 and 15 days post-agroinfiltration.

A primer set was used for PCR amplification using high fidelity Phusion polymerase, a fragment flanking IR region of TYLCV (FIG. 6). PCR products were gel purified and 200 ng was subjected to SspI restriction enzyme protection analysis to detect the presence of indels. The SspI digested product was separated on 2% agarose gel. The PCR product was cloned to pJet2.1 vector and subjected to Sanger sequencing.

Example 5

T7EI mutation detection assay: To determine and quantify the activity of the CRISPR/Cas9 system on TYLCV genome, the mutations resulting from the DSB repair through the NHEJ pathway were measured in Ali Z, et al., (2015) Mol. Plant March 6. S1674-2052, incorporated herein by reference in its entirety). Briefly, genomic DNA was prepared from samples collected after 5, 10, and 30 days and used as a template for PCR amplifications of fragments encompassing the target sequences (Table 1). PCR amplicons were denatured and then renatured. Subsequently, to calculate the frequency of modification, the samples were denatured and renatured, and treated with T7EI. ImageJ software was used to calculate the mutation rates.

Example 6

Rolling circle amplification: Total genomic DNA extracted from plants and quantified by Nano Drop® and was adjusted to 50 ng/μL. The rolling circle amplification amplicon kit (GE Health Care) was used to perform experiments with total genomic DNA. Genomic DNA (50 ng) was incubated for three mins at 95° C. in sample buffer and placed on ice for 5 mins. Enzyme mix and reaction buffer were added to the samples and placed at 30° C. for 18 hours for amplification and 65° C. for 15 mins to inactivate the enzyme. Then NcoI was added to the samples and incubated for 1 h at 37° C. The DNA samples were resolved on 1% agarose gel.

Example 6

Southern blotting analysis: A 560 bp-DIG labeled probe specific to TYLCV sequence was prepared by PCR amplification of the region flanking the IR using a primer set.

Total genomic DNA (2 μg) extracted from *N. benthamiana* plants was resolved on a 1% gel. The DIG-labelled size marker DIG marker-11 (Roche) was also run at one end of the gel. The DIG-labeled size marker (DIG marker-11, Roche) was used to show the linear dsDNA of TYLCV. Gel picture was taken under UV and the DNA bands were transferred to nylon membrane (Roche). Subsequently, membrane was hybridized with DIG-labelled probe and DNA bands corresponding to TYLCV were visualized using anti-DIG-alkaline phosphatase (1:10,000) and CPD chemiluminescent substrate using alpha Innotech digital imaging system.

Example 7

DNA blot analysis: PCR amplicons of IR-specific fragments of CLCuKoV and TYLCSV were DIG-labeled. Total genomic DNA (2 μg) from *N. benthamiana* plants was electrophoresed in 1% gels alongside the DIG-labeled size marker DIG marker-II (Roche). The DNA fragments were blotted onto a nylon membrane (Roche), followed by UV-crosslinking and hybridization with the respective IR-DIG-labeled probes. DNA bands were visualized using alkaline phosphatase-conjugated anti-DIG (1:10,000) and CPD chemiluminescent substrate in an Alpha Innotech digital imaging system.

Example 8

TRV-mediated delivery of sgRNA: TRV was used for the delivery and expression of sgRNAs with different target specificities as described previously[7,30]. To systemically deliver the sgRNAs, cloned TRV vectors were agroinfected into Cas9OE *N. benthamiana* plants for targeting of the TYLCSV, CLCuKoV, MeMV DNA-A, and MeMV DNA-B genomes, respectively. Seven days post TRV-mediated sgRNA delivery, a second leaf was infiltrated individually with *agrobacterium* containing infectious clones of TYLCSV, CLCuKoV with CLCuMB, and MeMV DNA-A with MeMV DNA-B. Fifteen days post-DNA viral challenge, systemic leaves were collected for molecular analysis.

Example 9

CRISPR/Cas9 evasion analysis of TYLCV2.3 and TYLCSV via sap transmission: TYLCV2.3 and TYLCSV sap inoculation was conducted as described by Gilbertson et al. (1991), with slight modifications. Briefly, two-week-old WT *N. benthamiana* plants were inoculated with sap extracted from TYLCSV-infected (CRISPR/Cas9 targeted) systemic leaves. The leaves were ground to a powder and re-suspended at 1:4 (w/v) dilution in potassium phosphate buffer (0.1 M, pH 8.0). The sap (from TYLCSV targeted at the IR or CP) was then applied to WT *N. benthamiana* plants. The adaxial surfaces of three leaves and pedicels were dusted with carborundum (200-450 mesh) and thoroughly rubbed with sap using a pestle. The leaf pedicels and main stem were also injected with the same sap using an 18-gauge needle. The top (young) systemic leaves were collected at 15 days after sap application and DNA was extracted. The extracted DNA was directly used for molecular analysis or enriched to detect the presence of indels by pretreatment with the respective enzymes. T7EI and restriction site loss were used for the detection of CRISPR/Cas9 evasion, and Sanger sequencing was used to identify the modified sequences of the viral escapees. These experiments were performed for the noncoding (IR) and coding (CP) viral regions.

Example 10

CRISPR/Cas9 evasion analysis of CLCuKoV via grafting: Scions from four-week-old WT *N. benthamiana* plants were grafted onto stocks of plants infected with CLCuKoV and CLCuMB and targeted at the IR and CP by CRISPR/Cas9 for 15 days. Top (young) leaves of scions were collected at 21 days after graft establishment and used for extraction of total genomic DNA. The extracted DNA was enriched for indels by pretreatment with the respective restriction enzymes, followed by use as a PCR template to amplify the IR or CP targets. Molecular analysis was performed for mutation detection as described above.

Example 11

To construct this viral-mediated genome editing system, Cas9-over-expressing lines of *Nicotiana benthamiana* were generated. First, the human codon-optimized Cas9 sequence was optimized for in planta expression by generating the pK2GW7.Cas9 clone, and then *Agrobacterium tumefaciens* was used to transform tobacco leaf discs. The Cas9 clone was sequence verified, and its proper localization confirmed by transient expression of a GFP-fusion variant (encoded by pEARLYgate103.35S:Cas9:GFP) in tobacco leaves. In addition, the transgenic tobacco plants were analyzed at the molecular level to determine the expression levels of the Cas9 transcript and protein.

Next, a TRV RNA2 genome-derived vector was constructed and optimized for sgRNA delivery. The TRV RNA2 constructs contained the sgRNA under the control of either of two sequences: the *Arabidopsis thaliana* RNA polymerase III-transcribed U6 promoter (U6::sgRNA) as a control, or the PEBV promoter (PEBV::sgRNA) to permit the expression of the sgRNA from the viral RNA-dependent RNA polymerase.

The TRV virus was reconstituted in tobacco leaves by agroinfiltration of mixed *Agrobacterium* cultures harboring the RNA1 genome (pYL192) in combination with the different RNA2 vectors in which an sgRNA with binding specificity for the phytoene desaturase (PDS) gene was driven by the negative-control promoter (pYL156.U6:: PDS.sgRNA) or the PEBV promoter (pSPDK.PEBV:: PDS.sgRNA). Ten days post-infiltration, the presence of the TRV RNA1 and RNA2 genomes in both the inoculated and the systemic leaves was confirmed by RT-PCR. Assays were then performed for genomic editing of the target sequence in both inoculated and systemic leaves using the surveyor and T7EI nucleases and restriction-protection analysis. Significant levels of editing in both assays were detected. In both types of leaves, editing efficiencies were higher than those reported in previous studies. Furthermore, to corroborate the T7EI and restriction-protection assays, the target sequence from both inoculated and systemic leaves were PCR-cloned. Thirty of the resultant clones were then subjected to Sanger sequencing analysis. The sequencing analyses confirmed the results of the T7EI and restriction-protection assays, and demonstrated that modification ratios were high: indels were present in 17 clones derived from inoculated leaves and in 9 clones from systemic leaves.

It is to be understood that the viral-mediated genome editing platform of the disclosure is not to be limited to vectors derived from TRV; other RNA viruses (e.g., tobacco mosaic virus and potato virus X) can also be used to deliver sgRNA molecules to various plant species. For genome editing purposes, TRV is most advantageous as a vehicle for sgRNA delivery to all plant parts, including meristems. The ability of the virus to infect growing points can lead to modification of the germline cells and eventually to seeds with the desired modifications, obviating the need for tissue culture and transformation. In addition, this system could be applied to transcriptional gene silencing by delivering sgRNAs that target promoter regions into plants overexpressing a catalytically inactive Cas9 endonuclease.

Accordingly, the viral-mediated genome editing systems of the disclosure meet several requirements for efficient and multiplexed editing: 1) TRV can systematically infect a large number of plant species, both naturally and under laboratory conditions; 2) the virus is easily introduced into plants via *Agrobacterium* and delivery into growing points of the plant; 3) the small genome size of TRV facilitates cloning, multiplexing, library constructions, and agroinfections; and 4) the viral RNA genome does not integrate into plant genomes.

TABLE 2

| PRIMER NAME | SEQUENCE (5'-3') | Usage |
|---|---|---|
| Cas9-gw-Fw | CACCATGGACTATAAGGACCACG (SEQ ID NO: 102) | To clone cas9 |
| Cas9-Rev-Stop | TTACTTTTTCTTTTTTGCCTGGC (SEQ ID NO: 103) | To clone Cas9 |
| Cas9-Rev-No-Stop | CTTTTTCTTTTTTGCCTGGC (SEQ ID NO: 104) | To make Cas9-GFP |
| NB-ACTIN1-RT-F | TGAAGATCCTCACAGAGCGTGG (SEQ ID NO: 105) | Rt-pcr normalization control |
| NB-ACTIN1QRT-LIU-R | TTGTATGTGGTCTCGTGGATTC (SEQ ID NO: 106) | |
| CAS9-SEQ-F6 | GCCCTCCAAATATGTGACTTCC (SEQ ID NO: 107) | Cas9 expression confirmation |
| CAS9-REV-STOP | TTACTTTTTCTTTTTTGCCTGGC (SEQ ID NO: 108) | |
| TRV1-RELICASE-RT-F | CTACTGGGAGAGCAGCAACC (SEQ ID NO: 109) | For detection of trv-rna1 systemic movement |
| TRV1-REPLICASE-RT-R | CTGAGCGCAAAAGTACACCA (SEQ ID NO: 110) | |
| SPDK-PEBVS/SEQF | CGAATTCGAGCATCTTGTTCTGG GGTTTCA (SEQ ID NO: 111) | For detection of trv-rna2 sgRNA part systemic movement |
| SPDK-SEQ-R | CTATGGTAAGACAATGAGTCGGC CAAACGC (SEQ ID NO: 112) | |
| NB-PDS3-TR1,2-GDNA-F2 | GAAACACATCACCTAGGCGG (SEQ ID NO: 113) | For PCR around pds target |
| NB-PDS3-TR1,2-GDNA-R | GGGCGTGAGGAAGTACGAAA (SEQ ID NO: 114) | |
| NB.PCNA gDNA F1 | CCTAACCCTAATTTCCCCAG (SEQ ID NO: 115) | For PCR around pcna target |
| NB.PCNA gDNA R1 | TCACTGTCAATGTCCATCAG (SEQ ID NO: 116) | |

Example 12

The coding sequences of CLCuKoV are targeted for cleavage by CRISPR/Cas9 and subsequently repaired by NHEJ: The use of the CRISPR/Cas9 system to confer interference activities against monopartite plant DNA viruses was recently demonstrated (Ali et al., (2015) *Genome Biol.* 16: 1-11). The utility of the CRISPR/Cas9 system to confer molecular immunity against complex plant DNA viruses, i.e., viruses having partial or complete partite genomes was also explored using the monopartite virus Cotton Leaf Curl Kokhran Virus (CLCuKoV; AJ496286), which requires the helper betasatellite Cotton Leaf Curl Multan Betasatellite (CLCuMB) for symptom development (Mansoor et al., Arch. Virol. 148, 1969-1986 (2003)).

To deliver sgRNAs specific to the coding regions of the genes encoding the coat protein (CP) and the divalent cation coordination RCRII domain of replication associated protein (Rep) (FIG. 7A) of CLCuKov, the sgRNAs were delivered through Tobacco rattle virus (TRV) RNA2 into Cas9OE *Nicotiana benthamiana* plants. Next, the plants with an established sgRNA-Cas9 complex were challenged via agro-infiltration with infectious clones of CLCuKoV and CLCuMB. Total genomic DNA was next isolated from systemic leaves to investigate whether CRISPR/Cas9 could target and cleave the CLCuKoV genome and whether the DSBs generated by the CRISPR/Cas9 system would be repaired via NHEJ. The PCR amplicons encompassing the targets to T7 Endonuclease I (T7EI) were subjected to mutation detection analysis, where denatured DNAs are re-natured, then cleaved with T7EI, which degrades single-stranded regions of non-complementarity resulting from indels; these regions are then detected by sequencing.

High rates of indel formation were detected at both ORFs (18-49% in CP and 35-45% in RCRII) of CLCuKov (FIGS. 7B and 7D). Subsequently, the PCR amplicons were cloned into the pJet2.1 cloning vector and subjected them to Sanger sequencing to identify the nature of the modifications in the CLCuKoV genome. The results confirmed the presence of indels and indicated that Cas9 activity was high and was followed by NHEJ repair. All possible types of indels were observed (FIGS. 7C and 7E).

To investigate whether CRISPR/Cas9 could target the well-conserved IR of CLCuKov and whether cleavage results in the same rate of NHEJ repair, loss of a restriction enzyme recognition site was assayed. The invariant 9-nt conserved sequence in the IR contains a recognition site for SspI endonuclease and is located at the predicted Cas9 cleavage site, 3 bp upstream of the PAM sequence. The flanking 446-bp fragment encompassing the target sequence was digested with SspI. Complete SspI digestion of the wild-type (WT) sequence produced two fragments of 253 and 193 bp. Cas9 targeting and subsequent repair via NHEJ was expected to eliminate the SspI site within the conserved 9-nt sequence and thus generate a 446 bp fragment of SspI-resistant DNA. However, an SspI-resistant fragment was not detected in an agarose-based gel assay (FIG. 7F). Previously, it was found that multiple viruses can be targeted by a single sgRNA with an invariant sequence common to all geminiviruses (Gutierrez et al., EMBO J. 19, 792-799 (2000)).

Next, it was investigated whether CLCuKoV could be targeted by an invariant sgRNA. Different sgRNAs specific to the IRs of monopartite BCTV and TYLCV or bipartite MeMV against CLCuKoV were used. A restriction enzyme site loss assay did not reveal a significant level of indel formation.

Example 13

CRISPR/Cas9-mediated, efficient targeting of coding and non-coding sequences of MeMV: It was investigated whether the lack of NHEJ repair in the IR after CRISPR/Cas9 targeting is common in all partial or full bipartite viruses. The bipartite virus MeMV with genomic parts DNA-A and DNA-B were selected. sgRNA specific to the non-coding IR into plants was systemically delivered. The NB-Cas9OE plants were subsequently challenged via agro-infection with MeMV DNA-A and DNA-B. At 15 days post infection (dpi), PCR amplicons encompassing the IR target site were examined using the SspI enzyme loss assay. The SspI resistance results confirmed that, in contrast to CLCuKoV, CRISPR/Cas9 cleaved the stem loop sequence in the IR of MeMV, which was subsequently repaired by NHEJ (FIG. 8A). Sanger sequencing revealed the identity of the indel modification. In contrast to CLCuKoV, 13-19% of MeMV IRs were repaired by NHEJ, and all normal types of indels were produced (FIG. 8B). Notably, other types of modifications were also observed, albeit at low frequency, including long deletions. Consistent with this, multiple variants of IR-sgRNA targeted MeMV-A IR sequences with varying efficiencies (12-30%). As MeMV DNA-B has the same 20-nt sequence and can be targeted by the same sgRNA, the restriction site loss assay confirmed that, like MeMV DNA-A, MeMV DNA-B is targeted and repaired through NHEJ. Like the non-coding IR, targeting of the ORF sequences CP and RCRII of MeMV DNA-A produced high rates of indel formation (FIGS. 8C and 8E). However, in contrast to indels at the IR, the CP and RCRII regions of MeMV-A are only short indels produced by NHEJ. Long deletions at the targeted sites (FIGS. 8D and 8F) were not seen.

Example 14

Variable NHEJ repair efficiencies of IR sequences in different strains of TYLCV: In geminiviruses, the highly conserved nonanucleotide sequence is flanked by a stretch of short, complementary sequences, which form a stem-loop structure in the IR (FIG. 9A). This conserved structure is directly involved in virus replication as a site for Rep binding and nick formation, and has putative bidirectional promoters. Also, IRs are strain-specific and interact only with specific Rep proteins. The observation that the efficiency of CRISPR/Cas9 targeting or subsequent NHEJ repair differs between CLCuKoV and MeMV prompted an investigation as to whether this would be the case in different strains of TYLCV. Therefore, the authentic TYLCV2.3-IR-sgRNA was used to target TYLCV2.3 and the TYLCSV-IR-sgRNA to target TYLCSV. *N. benthamiana* plants over-expressing the CRISPR/Cas9 machinery were challenged with infectious clones of TYLCV2.3 and TYLCSV via agro-infection. At 15 dpi, the fragments encompassing the target sequences were PCR amplified and subjected the PCR amplicons to an SspI recognition site loss assay, which confirmed that the TYLCSV genome targeted by CRISPR/Cas9 was not subsequently repaired via NHEJ, i.e., detectable levels of indels (FIG. 9B) were not seen.

To exclude the possibility that the inability to detect any indels was due to a factor other than the inability of the CRISPR/Cas9 machinery to target the viral genome and to generate DSBs, the same machinery with the TYLCSV-sgRNA was used to target TYLCV2.3 and detected indel formation. The SspI recognition site loss assay confirmed that, like TYLCV2.3-IRsgRNA, TYLCSV-IRsgRNA could target the TYLCV2.3 genome, resulting in indel formation at the IR site of TYLCV (FIG. 9C). Moreover, no indels were detected after targeting TYLCSV IR with invariant sgRNAs. However, in contrast to the inability to detect indels at IRs of TYLCSV, higher frequencies of indel formation were observed in the ORFs encoding CP and the RCRII domain of Rep (71% for CP and 41% for RCRII) (FIG. 9D). These indels were produced through normal NHEJ repair.

Example 15

CRISPR/Cas9 targets the noncoding IRs of CLCuKoV and TYLCSV: To investigate the possibility that the CRISPR/Cas9 machinery targeted the CLCuKoV and TYLCSV genomes but that these genomes were neither repaired nor proficient in replication, DNA blot analysis was used to examine the total DNA from infected plants for the accumulation of CLCuKoV and TYLCSV genomic DNA. The results confirmed that compared to control plants, plants with the CRISPR/Cas9 machinery targeting the IR sequence accumulated lower levels of the CLCuKoV (FIG. 10A) and TYLCSV genomes (FIG. 10B).

The probe used to detect CLCuKoV also detected CLCuMB, but the amount of CLCuMB did not decrease as much as did CLCuKoV, which is consistent with the observation that the 20-nt target sequence in the IR (including the conserved nonanucleotide) of CLCuMB is not followed by a PAM (NGG). Nonetheless, indels were not detected in an agarose gel-based SspI site loss assay. Sanger sequencing of CLCuKoV IR, either targeted by its authentic IR-sgRNA or by an invariant IR-sgRNA, confirmed that CRISPR/Cas9 targeted the IR of the CLCuKoV genome, but the level of repair was extremely low (3%). Furthermore, the presence of only long deletions and a lack of the usual short indels was observed (FIG. 10C). Similarly, the results of sequencing indicated that targeting CLCuKoV with an invariant sgRNA occurred at a similar, low level (3%), and all targeted regions had long deletions, like those generated by the authentic IR-sgRNA against the CLCuKoV genome.

Example 16

NHEJ repair of the coding regions of geminivirus genomes facilitates the generation of protein variants and evasion of the CRISPR/Cas9 system: High rates of NHEJ repair (indels) were observed in the genomes of different geminiviruses after targeting the protein coding region or the non-coding regions (IRs) of TYLCV2.3 and MeMV. Investigated were: 1) whether indels created at these sites might allow the virus to evade the CRISPR/Cas9 machinery and if these viral variants would be considered escapees and 2) whether these escapees can replicate and produce a systemic infection. To address these questions, the sap from infected, CRISPR/Cas9-targeted plants (CP and IR of TYLCV2.3) was rub-inoculated onto leaves and directly injected into the leaf pedicels and stems of three-week-old WT *N. benthamiana* plants.

Samples were collected from the systemic top (young) leaves at 15 DAI. The respective CP and IR fragments were PCR amplified and subjected to T7EI and restriction site loss assays to detect mutations. The results indicate that some of the CP sequences repaired by NHEJ were capable of replication and systemic spreading in WT *N. benthamiana* (FIGS. 11A and 11B). To confirm the T7EI and restriction site loss assay results, Sanger sequencing was used to determine the identity of these indels. The results revealed the presence of indels in the target sequences of the viral genomes, indicating that they were escapee variants capable of replication (FIG. 11C). By contrast, detect any indels (escapees) in the IR samples were not seen.

To confirm that targeting a protein coding sequence of other geminiviruses could lead to similar CRISPR/Cas9 escapees, experiments were performed using TYLCSV and CLCuKoV. For TYLCSV, the same sap inoculation method used for TYLCV2.3 was employed, but for CLCuKoV, a grafting method was used with scions from WT plants grafted onto CRISPR/Cas9 CLCuKoV plants. Subsequently, total DNA was extracted at 21 dpi and PCR amplicons encompassing the target sequences were subjected to T7EI assays. The T7EI results confirm the presence of the modified (CP) genomes in samples from both CLCuKoV (FIG. 11D) and TYLCSV (FIG. 11E). The modified indels in the CP of CLCuKoV were also confirmed by Sanger sequencing of the PCR-amplified fragments. Furthermore, unlike the CP, a mutated IR in either the T7EI or restriction site loss assay was not seen.

Finally, it was investigated whether the rare genomic molecules with large deletions in the IR would be capable of replication or systemic spreading. These IR molecules were not detected in systemic leaves, indicating that they were unable to replicate or that they replicated at levels too low to be detected.

What is claimed:

1. A genetically modified plant resistant to at least one pathogenic geminivirus species, said plant comprising a heterologous CRISPR/Cas9 system and at least one heterologous nucleotide sequence as set forth in SEQ ID NO: 75, wherein the at least one heterologous nucleotide sequence directs inactivation of the pathogenic virus species or plurality of viral species by the CRISPR/Cas9 system.

2. The plant of claim 1, wherein the at least one heterologous nucleotide sequence is inserted into a chromosome of the plant, is an extrachromosomal element, or is inserted in a vector.

3. The plant of claim 1, wherein the pathogenic virus is of the geminiviridae genus *Becurtovirus, Begomovirus, Curtovirus, Eragrovirus, Mastrevirus, Topocuvirus* or *Turncurtovirus*.

4. The plant of claim 3, wherein the at least one pathogenic virus is selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV).

5. The plant of claim 1, wherein the plant is a tobacco plant or a tomato plant.

6. The genetically modified plant of claim 1, wherein the plant is a tobacco plant or a tomato plant, and said plant is resistant to at least one pathogenic geminivirus species selected from the group consisting of: Beet Curly Top Iran Virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV), and wherein the at least one heterologous nucleotide sequence is inserted into a chromosome of the plant, is an extrachromosomal element, or is inserted in a vector.

7. A method of generating a genetically modified plant resistant to a virus pathogen, the method comprising the steps of:
  (a) obtaining a plant susceptible to a pathogenic virus, wherein said plant is genetically modified to express a heterologous CRISPR/Cas9 system; and
  (b) genetically modifying said plant to have at least one heterologous nucleotide sequence as set forth in SEQ ID NO: 75, wherein the at least one heterologous nucleotide sequence can direct inactivation of the virus pathogen by the CRISPR/Cas9 system.

8. The method of claim 7, wherein step (b) comprises delivering the at least one heterologous nucleotide sequence to a population of cells of the plant by transfection with viral vector, by a mechanical method, or by genetically modifying an isolated plant cell and generating the plant therefrom.

9. The method of claim 8, further comprising the step of cultivating the genetically modified plant resistant to a virus pathogen to generate a population of said plants, wherein said progeny are reproduced sexually or asexually.

10. The method of claim 9, wherein the pathogenic virus is of the geminiviridae genus *Becurtovirus, Begomovirus, Curtovirus, Eragrovirus, Mastrevirus, Topocuvirus* or *Turncurtovirus*.

11. The method of claim 10, wherein the pathogenic virus is selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV).

12. The method of claim 7, wherein the plant is a tobacco plant or a tomato plant.

13. A method of generating a genetically modified plant resistant to a virus pathogen, the method comprising the steps of:
  (a) obtaining a plant susceptible to a pathogenic geminivirus of the geminiviridae genus *Becurtovirus, Begomovirus, Curtovirus, Eragrovirus, Mastrevirus, Topocuvirus* or *Turncurtovirus*, and wherein said plant is genetically modified to express a heterologous CRISPR/Cas9 system;
  (b) genetically modifying said plant to have at least one heterologous nucleotide sequence as set forth in SEQ ID NO: 75, wherein said at least one heterologous nucleotide sequence can direct cleavage of the virus pathogen by the CRISPR/Cas9 system, wherein step (b) comprises delivering the at least one heterologous nucleotide sequence to a population of cells of the plant by transfection with viral vector, by a mechanical method, or by genetically modifying an isolated plant cell and generating the plant therefrom; and
  (c) cultivating the genetically modified plant resistant to a virus pathogen to generate a population of progenies of said plants, wherein said progeny are reproduced sexually or asexually.

14. The method of claim 13, wherein the pathogenic virus is selected from the group consisting of: Beet Curly Top Iran virus, Spinach Severe Curly Top Virus, Bean Golden Mosaic Virus, Beet Curly Top Virus, *Eragrostis curvula* Streak Virus, Maize Streak Virus, Tomato Pseudo-Curly Top Virus, Turnip Curly Top Virus, and Tomato Yellow Leaf Curl Virus (TYLCV), and wherein the plant is a tobacco plant or a tomato plant.

15. The method of claim 14, wherein the pathogenic virus is Tomato Yellow Leaf Curl Virus (TYLCV).

* * * * *